US009526254B2

(12) United States Patent
Sadler-Bridge et al.

(10) Patent No.: US 9,526,254 B2
(45) Date of Patent: Dec. 27, 2016

(54) PESTICIDE AND REPELLANT

(75) Inventors: David Sadler-Bridge, Thetford (GB); Murree Groom, Thetford (GB)

(73) Assignee: ECOSPRAY LIMITED, Thetford (GB)

( * ) Notice: Subject to any disclaimer, the term of this patent is extended or adjusted under 35 U.S.C. 154(b) by 2110 days.

(21) Appl. No.: 11/911,023

(22) PCT Filed: Apr. 10, 2006

(86) PCT No.: PCT/GB2006/001290
§ 371 (c)(1),
(2), (4) Date: Oct. 9, 2007

(87) PCT Pub. No.: WO2006/109028
PCT Pub. Date: Oct. 19, 2006

(65) Prior Publication Data
US 2009/0317500 A1    Dec. 24, 2009

(30) Foreign Application Priority Data

Apr. 9, 2005 (GB) .................................. 0507227.7

(51) Int. Cl.
*A01N 65/42* (2009.01)
(52) U.S. Cl.
CPC ..................... *A01N 65/42* (2013.01)
(58) Field of Classification Search
None
See application file for complete search history.

(56) References Cited

U.S. PATENT DOCUMENTS

| 1,619,826 | A | * | 3/1927 | Marx |
| 3,139,346 | A | * | 6/1964 | Meusel ................... A23L 1/231 426/250 |
| 4,741,914 | A | * | 5/1988 | Kimizuka et al. |
| 4,876,090 | A | * | 10/1989 | Weisler |
| 4,959,237 | A | * | 9/1990 | Walker |
| 5,231,114 | A | * | 7/1993 | Awazu et al. |
| 5,429,817 | A | * | 7/1995 | McKenzie |
| 5,733,552 | A | | 3/1998 | Anderson et al. |
| 6,691,454 | B1 | * | 2/2004 | Conroy |
| 6,864,276 | B2 | * | 3/2005 | Fischer et al. |
| 2004/0220282 | A1 | * | 11/2004 | La Torre |
| 2006/0088627 | A1 | * | 4/2006 | Bartnick ................ A23F 3/163 426/52 |
| 2007/0036875 | A1 | * | 2/2007 | Bennett et al. |

FOREIGN PATENT DOCUMENTS

| BE | 903756 | A | * | 6/1986 |
| CA | 2148338 | A | * | 11/1996 |
| CN | 1349745 | A | * | 5/2002 |
| CN | 1372840 | | | 10/2002 |
| DE | 202005004632 | | | 6/2005 |
| EP | 0945066 | | | 9/1999 |
| GB | 1 337 205 | | * | 11/1973 |
| JP | 58004726 | | | 6/1981 |
| JP | 57192318 | A | * | 11/1982 |
| JP | 59196064 | A | * | 11/1984 |
| KR | 20010010239 | | | 7/1999 |
| WO | 03/059071 | | | 7/2003 |
| WO | 2005/055713 | | | 6/2005 |

OTHER PUBLICATIONS

Block, E. Sci. Am. (2985); 252(3): 114-9. The chemistry of garlic and onions.*
Tsao, S-M et al. J Med Microbiol. (2001); 50: 646-649. In-vito antimicrobial activity of four diallyl sulphides occurring naturally in garlic and Chinese leeks.*
Hile, AG et al. J Agric Food Chem (Mar. 26, 2004): 52(8): 2192-2196. Aversion of European Starlings (*Sturnus vulgaris*) to garlic oil treated granules: garlic oil as an avian repellent, garlic oil analysis by nuclear magnetic resonance spectroscopy.*
O'Gara, EA et al. Applied and Environmental Microbiology (2000); 66(5): 2269-2273. Activities of garlic oil, powder and their diallyl constituents against Helicobacter pylori.*
Heath. Source Book of Flavors. Van Nostrand Reinhold, USA 1981, pp. 153. "Garlic Oleoresin".*
U1; Mason, JR et al. Crop Protection (1997): 16(2): 107-108. Repellency of garlic extract to European starlings.*
Kyung, K. H. et al., Journal of Food and Science (Mar. 2002), 67(2): 780-785. Alliinase-independent inhibition of *Staphylococcus aureus* B33 by heated garlic.*
Amonkar, SV et al. Science (1971) ;174: 1343-1344. Isolation and characterization of larvicidal principle of garlic.*
X1; Deb-Kirtaniya, S et al. Indian J Agric Sci. 50(6): 507-509. 1980. Extracts of garlic as possible sources of insecticides.*
Reena and Ram Singh, "Insecticidal Properties of Garlic, Allium Sativum—a review", Journal of Medicinal and Aromatic Plant Sciences 25, Feb. 18, 2003, pp. 1024-1038.
Mason and Linz, "Repellency of garlic extract to European starlings", Crop Protection vol. 16 No. 2; Aug. 1997, pp. 107-108.
Deb-Kirtaniya et al., "Extracts of Garlic as possible source of insecticides", Indian J. agric. Sci. 50 (6); Jun. 1980, 4 pages.
Gupta et al., "Nematicidal properties of garlic, *Allium sativum* L.", Indian Journal of Nematology vol. 21, Issue 1; 1991, Abstract only.
Calvo-Gomez et al., "Solid-phase microextraction-gas chromatographic mass spectrometric analysis of garlic oil obtained by hydroistillation", Journal of Chromatography A, 1036; 2004, 2 pages.
Calvey et al., "Allium Chemistry: Supercritical fluid extraction and LC-APCI-MS of thiosulfinates and related compounds from homogenates of garlic, onion, and ramp. Identification in garlic and ramp and synthesis of 1-propanesulfinothioic acid S-allyl ester", J. Agric. Food Chem. 1997, 45, pp. 4406-4413.
Staba E.J. et al., "A commentary on the effects of Garlic extraction and Formulation on Product Composition", American Society for Nutritional Sciences; 2001, 2 pages.

(Continued)

*Primary Examiner* — Susan Hoffman
(74) *Attorney, Agent, or Firm* — Cantor Colburn LLP

(57) ABSTRACT

A pesticide or repellent comprising a liquid concentrate obtained from garlic juice by the removal of water from the juice.

6 Claims, 6 Drawing Sheets

(56) References Cited

OTHER PUBLICATIONS

Pozharitskaya O N et al. "Influence of extraction's parameters on the content of sulfur compounds in *Allium sativum* L. oil extracts from onions and some features of their determination", Rastitel'nye Resursy; 2001, Abstract only.

Allium S E, "Natural Garlic Barrier Ag for Natural Insect Control", Allium S.E.; 1997, 4 pages.
Search Report for corresponding Application No. PCT/GB2006/001290 (WO 2006/109028), mailed Aug. 2, 2006.

* cited by examiner

Figure 9 (Chromatogram 1)
Garlic Oil Gold Standard 2.5µl injection (1:10 diluted oil) – Used as Retention Time and Peak Shape Reference Material
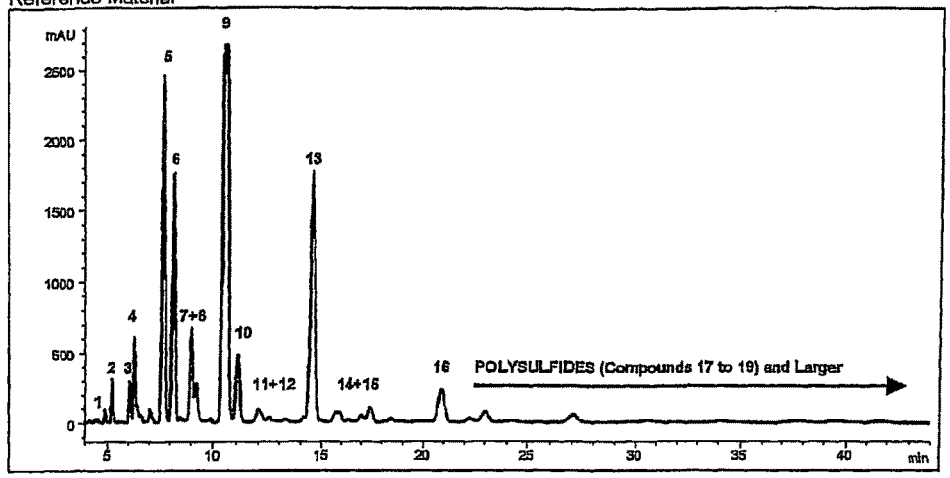
Figure 10 (Chromatogram 2)
RBSULF3 Garlic Standard (5µl 1:10)
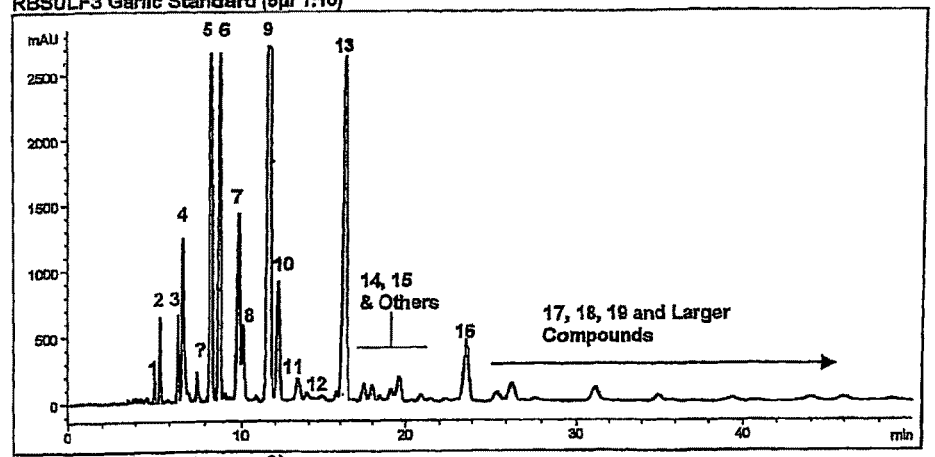
Figure 11 (Chromatogram 3)
RBSULF3 Garlic Product (5µl 1:10)
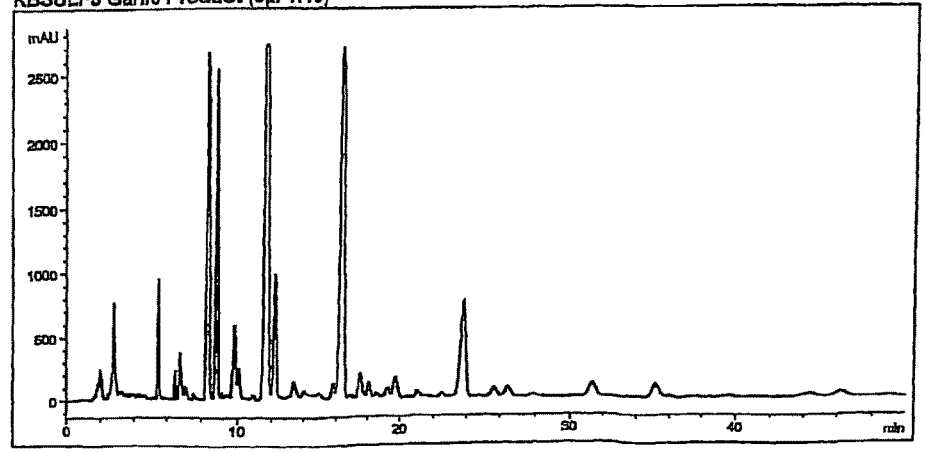

PESTICIDE AND REPELLANT

This application is a national phase of International Application No. PCT/GB2006/001290 filed Apr. 10, 2006 and published in the English language.

FIELD OF THE INVENTION

The present invention relates to the use of materials as insecticides, nemotocides and molluscocides and specifically to the use of a concentrate obtained from garlic for these purposes.

REVIEW OF THE ART KNOWN TO THE APPLICANT

The European Union's review of pesticide active ingredients is expected to lead to the removal of over 66% of the presently approved active substances by 2007. There is therefore a need for new more environmentally friendly pesticides.

The use of garlic oil as a avian repellent has previously been reported by Eric Block et al in the Journal of Agricultural and Food Chemistry, Volume 5, No. 8, pages 2192 to 2196 (1). Garlic derived preparations showing insect repellent activity and the toxicity of garlic to mosquito and other insect larvae have also been reported, see E Block, et al, Angew Chem. Int. Ed. Engl. 1992, 31, 1135-1178 (2); Kadota, Y. Insect repellents made from plant and herb extracts, JP 2003192516, 2003 (Chem. Abstr. 2003, 139, 48654) (3); and Bhuyan, M.; Saxena, B. N.; Rao, K. M. Repellent Property of Oil Fraction of Garlic, *Allium* Sativum Linn. Ind. J. Exp. Biol. 1974, 12, 575-6 (4). Additional references are made in reference (1) to garlic derived preparations having repellent activity towards small animals and also that topical applications of garlic reduced Northern Fowlmite infestations in laying hens. The nematocidal activity of allicin, an extract from garlic, has also been reported in International Journal of Pest Management, 1993, 39(4), 390-392 (5). The molluscicidal properties of garlic have also been reported, D. K. Singh and A. Singh. *Allium* sativum (garlic), A potent new molluscicide, Biological Agriculture and Horticulture, Vol. 9, No. 2 (6). A review of the antimicrobial properties of allicin are reported by S. Ankri and D. Mirelman in Microbes and Infection, 1999, 125-129 (7).

An article in the Journal of Medicinal and Aromatic Plant Sciences 2003, 25, PP. 1024-1038, titled "Insecticidal Properties of Garlic", Singh et al details various conventional methods of preparing garlic extracts such as water extraction, solvent extraction and also details the use of steam distillation to obtain garlic oil.

An article in the Indian J. Agric. Sciences 1980, 50, PP. 507-510 titled "Extracts of garlic as possible sources of insecticides" details the use of garlic oil obtained by steam distillation from minced garlic cloves; the use of a methanolic extract from garlic; and the use of water and ether extracts obtained when minced garlic was squeezed through a piece of muslin—as insecticides against *Spodoptera litura, Euproctis* sp. and *Culex* sp.

The abstract for an article in the Ind. J. Nematology 1991, 21, pp. 14-18 (Gupta et al) refers to the use of an aqueous extract of garlic which has nematocidal properties. Reference is also made to the use of a distilled oil fraction of garlic which is said to be toxic against nematode lava. Furthermore the abstract details the use of clove powder as a nematocide.

US Patent Application: U.S. Pat. No. 5,733,552 patent details the use of a dilute garlic juice on grass, shrubs and trees as a means of repelling mosquitoes.

European Patent Application: EP0945066A1 relates to the use of a mixture of garlic oil or extract which is combined with essential oils to give an improved insecticide/fungicide.

There are problems associated with the production of garlic oil as it requires a separation of the oil from the natural juice. This normally involves the garlic being crushed and heated to 100° C. in order to carry out a steam distillation. The garlic oil is then separated from an aqueous phase on cooling.

There are also certain problems inherent with the use of garlic oil, as garlic oil at room temperature is a viscous liquid which is difficult to dilute requiring the use of a carrier solvent which also has to be miscible with the liquid being used as a diluent. The use of such carrier solvents restricts the use of garlic oil in organic farming and introduces other difficulties related to the health and safety aspects associated with the use of such solvents.

It is therefore advantageous if, rather than isolating the oil from garlic as previously described, the garlic is simply crushed and the juice thus produced used directly. Unfortunately garlic juice isolated in this manner is prone to decomposition through a combination of chemical degradation and microbiological activity. The sulphur components of the garlic juice presumably being oxidised to sulphur dioxide/sulphur and the organic components being oxidised/hydrolysed to ketones or degraded to carbon dioxide through respiration. As such, if the extracted garlic juice is to be used, it must be freshly isolated from garlic and used almost immediately in order to ensure maximum efficacy as a pesticide/biocide. A markedly decreased level of activity of the material as a repellent may be retained after storage.

It would therefore be advantageous if a material could be provided which had the properties associated with garlic oil/fresh garlic extract in terms of its repellency to various life forms and its action as a pesticide, but which did not require the steam distillation stage involved in the isolation of the garlic oil. Such a material is described herein together with a process for the production of that material.

BACKGROUND

The properties of garlic oil and garlic extracts, as described above, are believed to be derived from the presence of allyl polysulphides which are produced following the rupture of the cell walls of garlic during the crushing process. In this process, alliin is converted to allicin by an enzyme called allinase. Subsequently the allicin breaks down to form polysulphides as shown in scheme 1.

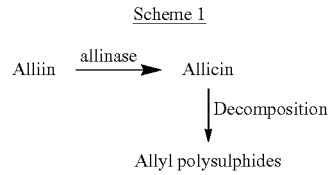

Scheme 1

It is the allypolysulphides that are believed to give garlic extracts and garlic oil their biological activity and repellency properties. This biological activity of garlic is believed to be due to the allyl polysulphides acting as enzyme inhibitors, metal sequestrants, solvents which are active on cell membranes, respiratory inhibitors and as general antibiotics.

SUMMARY OF THE INVENTION

In its broadest aspect there is provided a pesticide comprising a liquid concentrate obtained from garlic juice by the removal of water from the juice. The concentrate disclosed herein has the properties associated with garlic oil/fresh garlic extract in terms of its repellency to various life forms and its action as a pesticide, but does not require the distillation stage involved in the isolation of the garlic oil and additionally is stable to long term storage without a decrease in the activity of the material. This stability is due, at least in part, to the removal of water from the extracted juice. This provides a concentrate which possess little or no free water which can be utilised by the living organisms normally responsible for the breakdown of the component parts of garlic juice that give it its biological activity.

Preferably the water is removed by reduced pressure distillation at a temperatures below 40° C. In this way decomposition of the of the component parts of the garlic extract is minimised during its concentration.

Preferably the concentrate has a Brix value between 60 and 80. It is the removal of water to give a concentrate with a Brix value in this range that provides the stability observed with respect to the concentrate of the invention disclosed herein.

Preferably the total poly-sulphides in the concentrate are in the range 2 to 4% w/w.

Preferably diallyl sulphides of the formula RSR, $RS_2R$, $RS_3R$ and $RS_4R$ account for 66%±10% by weight of the total poly-sulphides present (wherein R=allyl group). Preferably the diallyl sulphide:diallyl di-sulphide:diallyl tri-sulphide:diallyl tetrasulphide are present in the approximate ratio of 4%-5%:5%-8%:31%-38%:19%-22% as weight % of the total poly-sulphides present. A concentrate containing these components, and in these ratios provides a pesticide with a consistent biological activity that might otherwise be obtained due to natural variability of garlic bulbs. Concentrates from a range of feedstock material may be readily blended to achieve this composition.

Preferably the water is extracted by reverse osmosis.

In this way a process is provided in which the minimum amount of energy is expended to isolate the concentrate. Additionally the concentrate thus has maximum efficacy as a pesticide as the level of heating to which the concentrate is exposed is minimised.

Preferably further polysulphides are added to enrich the polysulphide content. Such addition of polysulphides is expected to improve the performance of the mixture as a pesticide, as a repellent and is also expected to improve the residence time of the mixture when applied under open air conditions.

Preferably the polysulphides are added in the form of garlic oil. Garlic oil is a particularly preferred form of polysulphides to be used for enrichment purposes due to the lack of water in the oil, the addition of materials containing water would destabilise the matrix of the concentrate reducing the stability of the material.

In a second broad aspect of the invention there is provided a process for the production of a pesticide in the form of a liquid concentrate obtained from garlic by the steps of:
crushing garlic
separating the solid material from the liquid produced
carrying out a heating stage on the liquid to pasteurise the liquid
and removing water from the liquid by reduced pressure distillation at a temperature of approximately 40° C. temperature.

Isolating and concentrating the garlic juice in this way gives a concentrate which has maximum efficacy as a pesticide and which additionally avoids the expenditure of energy associated with the high temperature distillation normally used to produce garlic oil.

More preferably the water is removed from the liquid at a temperature of less than 25° C. and at an appropriate reduced pressure. In this way the efficacy of the material produced as a pesticide can be further optimised.

In a particularly preferred aspect, the water is extracted by reverse osmosis. In this way a process is provided in which the minimum amount of energy is expended to isolate the concentrate. Additionally the concentrate thus has maximum efficacy as a pesticide as the level of heating to which the concentrate is exposed is minimised.

In a third broad aspect there is provide a pesticidal composition characterised in that it comprises a wood flour based granule impregnated with a liquid garlic concentrate as previously described. A pesticide is therefore provided which is based entirely on materials which occur naturally in garlic and the only residues left by the use of the pesticide are the same residues left by the growing of crops of leeks or garlic. However the use of the pesticide disclosed leaves residues at a much lower level than those observed by the growing of leek and garlic crops. Additionally impregnating a wood flour granule in this way is also believed to result in effectively further drying the concentrate and thus improving the time for which the concentrate maintains its activity. Also improves ease of handling of the material, and its longevity in the field.

The pesticidal composition in the form of the liquid concentrate or concentrate impregnated granules, as previously described, is particularly useful as an insecticide. It has been shown that the concentrate or impregnated granule disclosed is effective in controlling cabbage root fly and is toxic to mosquito larvae as well as other larvae. It is believed that these results demonstrate that these materials will be effective against a much wider range of insects which are known pests.

The pesticidal composition in the form of the liquid concentrate or concentrate impregnated granules, as previously described, is particularly useful as a nematocide. The garlic concentrate and impregnated granule disclosed have been found to be particularly effective against nematodes.

The pesticidal composition in the form of the liquid concentrate or concentrate impregnated granules, as previously described, is particularly useful as an avian repellent. Garlic based products have previously been shown to be effective as repellents to birds. It is therefore reasonable to assume that the liquid concentrate and/or concentrate impregnated granule disclosed herein will also show such activity, but with the additional benefits of the stability conferred by the concentrate matrix.

The pesticidal composition in the form of the liquid concentrate or concentrate impregnated granules, as previously described, is particularly useful as a rabbit repellent. Results included in the present disclosure show concentrate impregnated granule act as a repellent to rabbits and it therefore reasonable to assume that the concentrate will show the same activity.

The pesticidal composition in the form of the liquid concentrate or concentrate impregnated granules, as has previously described, may be used as an insect repellent.

A pesticidal composition characterised in that it comprises a wood flour based granule impregnated with liquid garlic oil. Results disclosed herein show the effectiveness of granules impregnated with the garlic concentrate of the present disclosure and so it is reasonable to assume that garlic oil impregnated onto a wood flour based granule would show similar activity. By impregnating garlic oil onto such a granule the handling of garlic oil would be simplified and the requirement for the use of solvents to used in the dispersion of garlic oil is also removed.

A pesticidal composition characterised in that it comprises a wood flour based granule impregnated with liquid extracted from freshly crushed garlic. Results disclosed herein show the effectiveness of granules impregnated with the garlic concentrate of the present disclosure and so it is reasonable to assume that liquid extracted from freshly crushed garlic impregnated onto a wood flour based granule would show similar activity. Additionally the extracted juice impregnated onto the wood flour will have improved stability against decomposition as a certain degree of the water will be tied up with the wood flour and further water will be removed by the drying process disclosed herein.

FIG. 9 is HPLC chromatogram of Gold Standard Garlic Oil.

FIG. 10 is HPLC chromatogram of Industry Standard Garlic oil.

FIG. 11 is HPLC chromatogram of garlic juice concentrate.

DESCRIPTION OF THE PREFERRED EMBODIMENT

Figure 1:
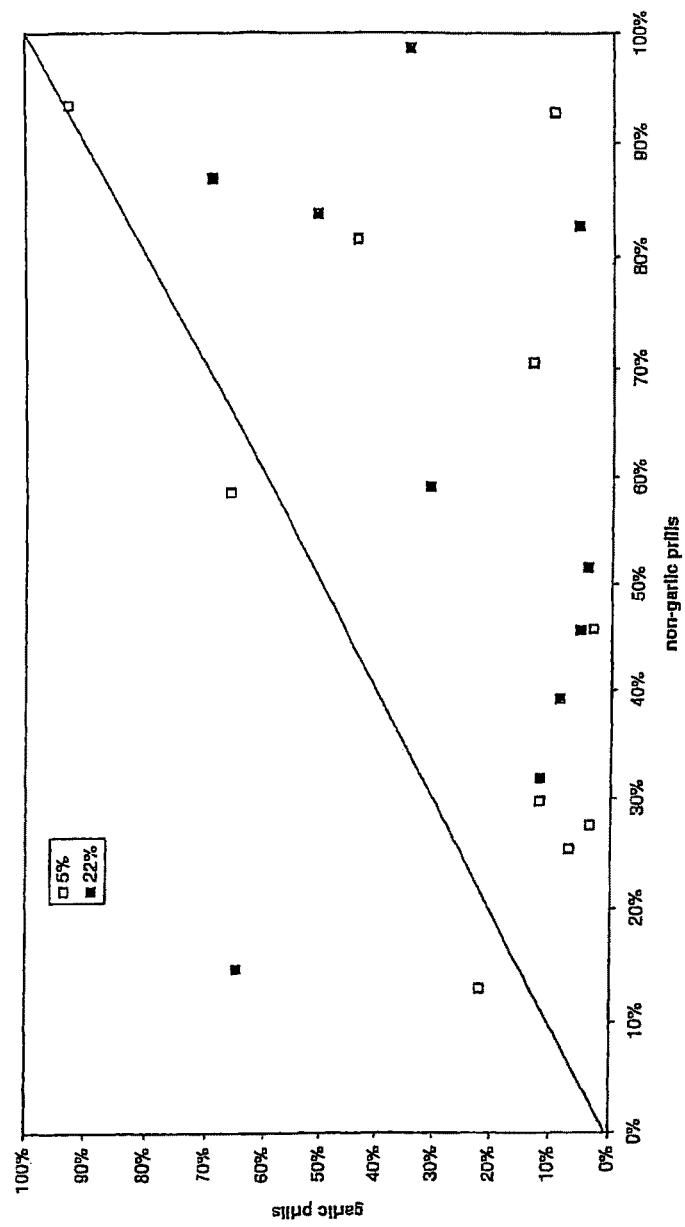
FIG. 1 shows a comparison of carrot eaten between feeding stations with prills impregnated or not impregnated with the garlic concentrate.

A concentrated garlic juice is produced according to the following method:
1) Fresh garlic is washed;
2) The garlic is crushed;
3) A pressing is carried out to separate solids from liquid;
4) The garlic juice is filtered (the filtration is normally carried out using a 50 micron filter);
5) A pasteurisation step is carried out, the juice is heated to a temperature of 90° C. for approximately 30 seconds or a lower temperature of 60° C. for a longer period of up to 2 minutes may be used;
6) A clarification step may then be carried out to remove any suspended material in the liquid;
7) Water is then removed by reduced vacuum distillation. This gives the concentrated garlic extract as a viscous brown liquid.

The water is removed by reduced pressure distillation at a temperature of less than 40° C., as this prevents decomposition of the components of the garlic concentrate and more preferably the pressure is reduced to a point such that the removal of water can be carried out at 25° C.

It is important to note that none of the prior art cited details the formation of a garlic juice concentrate wherein the water is removed from a garlic juice simply by reduced pressure distillation. All the prior art known to the applicant details the use of standard extraction techniques to isolate the active ingredients from the garlic juice by the use of water extraction, standard solvent extraction techniques or by the use steam distillation to obtain garlic oil.

Analysis of the concentrate produced by the above method gives analytical data in the following ranges:
Dry matter (brix); 60-80
pH (10%. Sol.): 4.0-5.0
Acidity (meq/kg): 300-400
(Equivalent to 2.1-2.8% of monohydrated citric acid)
Available carbohydrates 45-55%
1 kg of concentrate is equivalent to approximately 7 kg of fresh garlic HPLC Analysis The preferred method of analysis for determining the relative ratio of the diallyl polysulphides present in the concentrate is HPLC. Details of the HPLC methods used and the literature method on which they are based are provided in Appendix 1. The third method (RBSULF3) described in Appendix 1 which corresponds to method RBSULF1 with an extended equilibration time is the preferred HPLC method of analysis. A chromatogram obtained from a Garlic Oil Gold standard sample is provided (Chromatogram 1) with the main peaks of the chromatogram identified. Chromatogram 2 is also a chromatogram for a garlic standard. Also shown is a sample chromatogram for a garlic juice concentrate—labelled as—Garlic Product (Chromatogram 3).

Analysis of the concentrate by HPLC shows the total polysulphides present are in the range of 2.4 to 3.6% w/w. Of these polysulphides, diallyl sulphides of the formula RSR, $RS_2R$, $RS_3R$ and $RS_4R$ (R=allyl group of the formula —$CH_2CHCH_2$) are present in the approximate ratio of 4%-5%:5%-8%:31%-38%:19%-22% as weight % of the total poly-sulphides present. These poly-sulphides collectively account for approximately 66%±10% of all the organo-sulphur species present in the concentrate as determined by HPLC The concentrate produced by the above process therefore has a high degree of chemical similarity with respect to the polysulphides present in those materials that are found in the liquids produced by simply crushing and processing fresh garlic and to those present in garlic oil.

The biological activity of the garlic concentrate described herein is believed to be due to this particular ratio of diallyl- and methyl allyl-polysulphides.

The removal of water in the above manner to provide a garlic concentrate which maintains its stability when stored for prolonged period has clear advantages as compared to the process used to isolate garlic oil, or as compared to the juice obtained by simply crushing fresh garlic. It is believed that the concentrate produced by the above process will maintain activity as described below for at least 3 years, a much longer period that non-concentrated garlic juice. Samples of concentrate were analysed for a key active component, after storage under typical industry "temperature abuse" conditions, with the following results:

| Age of Concentrate | Total Polysulphide Concentration |
| --- | --- |
| 3 yr 10 months | 2.96 (% w/w) |
| 3 yr 2 months | 2.74 (% w/w) |
| 2 yr 9 months | 2.67 (% w/w) |
| 1 yr 4 months | 3.61 (% w/w) |

The consistency of these analytical results demonstrates the long-term stability of the product.

Heating of the extracted liquid to a temperature of 60-90° C. for a short period is believed to lead to the conversion of the allicin in the garlic extract being converted to polysulphides with the particular ratio of diallyl polysulphides described herein, this ratio has been found to be particularly effective in the applications described below.

Preparation of Granules Impregnated with the Garlic Concentrate

A granular form of the garlic concentrate has also been developed by the inventors. The granules are a formulation of the previously described garlic concentrate impregnated onto woodflour with a binder also present in the ratios shown in table 1 below. Unless otherwise stated, reference to woodflour granules impregnated with garlic concentrate is a reference to granules of the composition shown in table 1.

TABLE 1 showing the composition of the granules impregnated with garlic concentrate

| Chemical Name | CAS. No | Chemical Description | Trade Name | Function | Content (%) |
| --- | --- | --- | --- | --- | --- |
| Sodium carboxy-methyl cellulose | 9004-32-4 | High purity sodium carboxy-methyl cellulose (food grade) | Blonose | Binder | 1.65% |
| Woodflour | Lignin (9005-53-2) Cellulose (9004-34-6) | Association of cellulose, lignin and wood polyoses | Lignocel | Carrier | 53.35% |
| Garlic Oil | 800-78-0 | Garlic concentrate (food grade) | | Active ingredient | 45% |

The sodium carboxy-methyl cellulose, woodflour and garlic concentrate are mixed together such that they agglomerate into near spherical pellets/granules between 1 mm and 2 mm in diameter. The granules thus produced are yellowy brown in colour and have a very strong garlic/sulphur odour.

The granules are subsequently dried by use of warm air at approximately 60° C. for up to 2 hours. Subsequent HPLC analysis of the concentrate contained within the granule shows the same relative amounts of the four allyl sulphides, of the formula; RSR, $RS_2R$, $RS_3R$ and $RS_4R$ (R=ally group of the formula $CH_2$ CH $CH_2$), as were found by analysis carried out on the concentrate.

The efficacy of the granules is very dependant on moisture, see example 5 which relates to the use of such granules to control cabbage root fly (and includes results demonstrating this effect).

It is believed that forming granules in this way from the concentrate further stabilises the active components of the concentrate.

All of the trials described below were carried out in secret and under non-disclosure agreements.

Rabbit Repellency Trials using Garlic Granules

Non-public trials have been carried out which show that granules impregnated with garlic concentrate are effective as a rabbit repellent, see Example 1. These trials provide strong evidence that garlic granules/prills are effective at deterring rabbits from eating carrots when carrots free from garlic are also available, see Example 1. The granules/prills used in the trials were produced from woodflour impregnated with garlic at a level of 5% and/or 20% and, prepared as previously described Nematocidal Activity of the Garlic Concentrate The garlic concentrate of the present invention has been found to be effective as a nematocide. Initial in-vitro results established the toxicity of the concentrate to nematocides as shown in Example 2 and provided indications of the dilution of the garlic juice concentrate (referred to as NEMguard in Example 2) that should be used in field trials. When the garlic concentrate was used as a liquid formulation through trickle feed irrigation on potato crops, to protect against free living and cyst nematodes, a 14% increase in gross yield of the crop was observed following two applications of the garlic juice concentrate.

The garlic concentrate referred to as NEMguard has been found to kill almost all nemotocides present within 24 hours at a dilution of 0.05% v/v with water, with 0.1% v/v solution strength total kill can be achieved in 4 hours and with 0.25% v/v solution strength total kill can be achieved in 1 hour. Preferably the NEMguard should be mixed in with water at the end of a plant watering period, in this way elution of the product away from the primary target is reduced. Such treatments should ideally be carried out on a weekly basis during the growing cycle of the crop.

The critical period during which nematocides should be applied with respect to root crops is the first 4 to 5 week period post drilling. During this time, nematocides attack the delicate new root tip which leads to root forking and strutting with a consequential loss of quality and yield. The impact of free living nematocides can be such that entire crops become uneconomic to harvest.

The LD50 of NEMguard (the garlic concentrate) for free living nematocides has been identified as 0.025% v/v, and has nematocidal effects against both free living and cyst nematocides. The concentrate has been used to protect crops of potatoes, carrots, parsnips, strawberries and melons (n.b. PCN—Potato Cyst Nematode).

Details relating to the use of granules impregnated with the garlic concentrate referred to as NEMguard are provided in Example 3. The main body of evidence relating to effectiveness of the granules is derived from the use of granules applied through a seed drill with a standard granular applicator as described in Example 3.

Example 3 also includes reference to in-vitro test results, see 3.2, carried out by dissolving granules impregnated with garlic juice concentrate (referred to as ECOguard granules in section 3.2 of example 3) in water and then introducing specimens of various plant parasitic nematode species into the supernatant. Without exception all species of nematode were killed at solution strengths of 2.5 w/v % granule to water in 2 hours The reference in example 3 section 3.3 to NEMguard is a reference to the use of the garlic concentrate and shows efficacy, by the use of in-vitro tests, of the garlic concentrate against the nematode *Longidorus elongates* as well as other nematodes.

Example 3 sections 3.4 and 3.4.1 show the effectiveness of woodflour granules impregnated with the garlic concentrate against *Globedera pallida* (PCN-Potato Cyst Nematode).

Section 3.5.1, 3.5.2, 3.5.3 of Example 3, Example 3A and Example 3B show the effectiveness of woodflour impregnated granules at reducing the forking observed in carrot crops due to the effectiveness of the woodflour impregnated granules against carrot nematodes.

Example 4 provides further results relating to the effectiveness of woodflour granules impregnated with the garlic concentrate at reducing root forking in carrots due to the effectiveness of the granules in controlling carrot nematodes.

Also shown in Example 4 are results relating to the efficacy of a combined application of woodflour granules impregnated with garlic concentrate (NEMguard granules) and garlic concentrate/liquid (CL AIL 0021) for controlling Potato Cyst Nematode (PCN).

Further results in Example 4 show the effectiveness of woodflour granules impregnated with the garlic concentrate (referred to as ECOguard GR) and of the garlic concentrate (referred to as ECOguard SR and CL AIL 0021) in controlling root-knot nematode *Melioidogyne* spp., on orient-melon.

Results are presented in Example 4A showing the effectiveness of garlic impregnated granules (referred to as NEMguard®) at controlling a variety of nematode species i.e. *Longidorus elongatus, Pratylenchus crenatus, Tylenchorhynchus dubius* and *Paratrichodorus pachydermus*, in a field used for growing strawberries.

Cabbage Root Fly

The use of the granulated form of the concentrate referred to as ECOguard granules has been shown to provide significant reduction in cabbage root fly damage when used on crops of swede, see Example 5.

Spraying of Cabbage Root Fly eggs directly with a 1% solution of the garlic concentrate showed a lower rate of hatching of the eggs than a control sample of eggs which were not sprayed.

Poultry Red Mite

The garlic concentrate has also been found to act as a biocide for reduction of poultry red mite infestations. The concentrate has a particular advantage, as compared to compounds such as cypermethrin (sold under the trade name Barricade), in that it can be applied within buildings infested with red mite with the birds still within the building, but eggs should be removed before use. This is the first botanical biocide, known to the applicants, that has been shown to be effective at reducing poultry red mite infestations, at the recommended use rate the concentrate acts as a contact biocide.

The concentrate is particularly effective as a biocide when used in confined spaces or in mildly soiled environments.

Mortality levels in excess of 85% are normally observed in stimulated use studies and similar effects have been reported and observed from confidential field trials: see Example 6.

The concentrate also functions as a repellent and appears to inhibit recolonisation.

Conventional biocides tend to have single site action (acetylcholine esterase inhibition) and resistance to these compounds can build up quickly through selection and mutation in the population.

It is believed that the concentrate disclosed herein (referred to as Breck-a-sol) for use as a control means against Poultry Red Mite) has multi-site action, e.g.

Respiratory enzyme inhibition

Membrane disruption and depolarisation

Metal ion sequestration and chelating in cytosol

The likelihood of red mites building up resistance to the garlic concentrate is therefore lower due to the biochemical complexity of how the product functions as a biocide.

Environmental Impact

The increasing awareness of environmental issues in recent years has lead to the promotion of more environmentally friendly agricultural practices and to an increase in the production of food bearing the organic label. As such the provision of the garlic extract disclosed herein for use as a pesticide or repellent is a significant step forwards, as the decomposition products formed by the use of the extract are entirely natural, corresponding to the same materials left in soil after garlic or leeks have been grown but at a much lower level. Typically commercial crops of garlic and onion will release 120-600 times more polysulphides to soil than a 12 kg/ha application of Ecoguard granules, see reference (1). A detailed analysis of this assertion is provided in Appendix 2 wherein the garlic concentrate is referenced as AIL 0021 and CL AIL.

Enrichment of Garlic Juice Concentrate by the Addition of Garlic Oil.

The polysulphide mixture contained in the garlic juice concentrate of the present invention resembles the polysulphide mixture of distilled garlic oil. The polysulphide content of the garlic juice concentrate, produced according to the present invention, can therefore be enriched following its production by the addition of garlic oil. Enrichment of the polysulphide mixture of the garlic juice concentrate in this way gives a material which has an increased level of polysulphides whilst the properties of the garlic juice matrix continue to stabilise the resulting mixture with respect to long term storage. In this way the polysulphide content may be increased to in excess of 7% w/w. The increase in the level of polysulphides in the resulting mixture, is expected to improve the performance of the mixture as a pesticide, as a repellent and is also expected to improve the residence time of the mixture when applied under open air conditions.

The invention is defined by the claims that follow. It is believed that the pesticide, disclosed herein, is particularly efficacious with respect to its toxicity to mosquito larvae and other insect larvae as well as nematodes, aphids (Hemiptera), vine weevils, various beetles (Coleoptera), moths and butterflies (Lepidoptera), molluscs, mites and cabbage root fly. The material is especially effective as a nematocide.

In relation to its repellency, the material is particularly effective as a repellent to insects, rabbits and certain avian species.

Example 1

Rabbit Feeding Repellency Trials Using Garlic III

Introduction

Preliminary non-public experiments on group living rabbits demonstrated a significant effect of garlic as a rabbit feeding repellent. More detailed experiments were conducted on 20 individually housed rabbits. On this occasion, rabbits were selected at random to receive prills impregnated with garlic juice concentrate at levels of 5% or 22%. The prills impregnated with garlic juice concentrate were found to induce a significant repellent effect, although no significant difference in effectiveness was found between the two garlic concentrations.

Further non-public trials were conducted which were designed to examine the longevity of the garlic repellent response with age of prill. This report provides information on the experimental protocol and summarises the results of this trial.

Materials and Methods

The work was conducted on 20 captive rabbits of wild origin. Although normally penned in pairs, each rabbit was kept individually in three by two meter outdoor pens for five days prior to, and during the experiment. Each rabbit had access, at all times, to commercial pelleted rabbit food, as well as grass growing freely in each pen, and water ad libitum. Rabbits are primarily crepuscular feeders, and so the experiments took place between approximately 15:30 and 09:00 hours. The slightly longer exposure time in comparison to previous trials was unavoidable due to the short day lengths at this time of year.

Prior to the start of the experiment, prills from a newly opened packet, were pre-weighed when dry, to determine the average number of dry prills needed to stimulate a density of 12 Kg of prills per hectare per bowl. On average, this equated to 5 control prills (containing 0% garlic) and 6 test prills (impregnated with 5% garlic juice concentrate) per bowl.

Six weeks before the start of the experiment, newly opened packets of control and test prills were then allowed to 'weather' in separate pots outdoors. Labelled 23 cm plastic plant pots were filled to approximately 3 cm in depth with gravel, followed by approximately 8 cm of soil (John Innes number 2, soil base compost). The soil was firmed down by watering with approximately 200 ml of distilled water. This was allowed to drain away, and sufficient prills (~2 g) were scattered on top of the soil to ensure adequate numbers for the duration of the trial. The plant pots were then left outdoors for a period of 2 hours (i.e. fresh prills=0 weeks) or for 2, 4, 5 or 6 weeks until such time they were used in an experiment. Weathering over the 16 week period included exposure to sun, rain (see below) and temperatures ranging from −12° C. to 20° C.

| MONTH | ACTUAL RAINFALL (mm) >5 mm THAT FELL IN A SINGLE DAY | | | | NUMBER OF DAYS OF RAIN |
|---|---|---|---|---|---|
| From 12th September | 6.1 | 14.8 | 5.7 | 14.4 | 13 |
| October | 16.4 | 9.5 | 11.7 | 15.6 | 20 |
| November | 39.5 | 12.1 | 6.7 | 10.1 | 23 |
| To 27th December | 27.1 | 7.5 | 9.0 | | 16 |

Prior to the start of the trial and during non-experimental days, rabbits were presented regularly with sliced carrot to minimise neophobia. A two-choice test was used, with sliced carrot presented in two separate bowls, one with control prills and one with test prills; 200 g of carrot was presented in each bowl. Bowls were placed in separate feeding stations, located as far apart as possible within the pen to avoid garlic odour impacting upon the control. To avoid position effects, the siting of feeding stations and bowls was exchanged for the second night of the experiment.

There were 10 weeks of experiments altogether in this trial, although this did not include the six weeks of weathering of prills prior to the start of the experiment. To avoid habituation effects, each rabbit was tested for the 2 experimental days, once every two weeks. Each of the five ages of prills were tested on all 20 rabbits, i.e. each rabbit was tested five times. Prill ages were allocated to the rabbits using a randomised latin square design. The rabbit feeding experiments began on Oct. 24, 2000 and ended Dec. 28, 2000.

On the day of the experiment, the requisite number of weathered prills (to stimulate a rate of 12 Kg ha$^{-1}$) was placed onto a damp filter paper (moistened with 3 ml of distilled water) in a glazed earthenware bowl. A plastic coated wire mesh was placed into the bowl, to prevent the prills coming into direct contact with the carrot. This allowed odours from the prills to permeate through the carrot, and mimicked prills lying in close proximity but not in contact with those parts of the vegetation being consumed by rabbits in the field.

Results

The percentage of the total food that was eaten over the two days in each feeding station was calculated after subtracting carrot 'dregs' that had become inaccessible to the rabbits after falling through the plastic coated grid. An analysis of variance was carried out to investigate the effects of rabbit, week of testing and age of garlic juice concentrate impregnated prills on the total percentage of food eaten (over both feeding stations).

There was no evidence that the prill age had an effect on the overall quantity of food eaten (p=0.479). However, it was found the quantity of food eaten varied considerably between rabbits (d.f.=16; p<0.001), although there was no evidence that the total quantity of food eaten varied over the weeks (d.f.=16; p=0.104).

Individual variation between rabbits in the response to garlic juice concentrate impregnated prills is shown in FIG. 1. FIG. 1 shows a comparison of carrot eaten between feeding stations with prills impregnated with the garlic concentrate and with prills not impregnated with garlic concentrate. It was also noted that only when the prills were fresh was there a more consistent positive feeding response due to the presence of control rather than garlic juice concentrate impregnated prills.

For analysis of the effect of garlic, the percentage of carrot eaten at the station with garlic prills was subtracted from the percentage at the control station, to give the reduction in the percentage of carrot eaten due to garlic juice concentrate. The mean reduction in percentage of carrot eaten at the different ages of prill is given in the table below.

| | Prill age (weeks) | | | | |
|---|---|---|---|---|---|
| | 0 | 2 | 4 | 5 | 6 |
| Mean reduction in percentage of carrot eaten from garlic versus control bowl | 22.6% | 4.9% | 0.7% | 3.6% | 1.5% |

ANOVA indicated that there was strong evidence (p=0.007) that on average, the rabbits ate less carrot from the feeding station with garlic prills, on average when the prills were fresh, than when the prills were older. There was no evidence (p=0.5) that prills weathered two weeks or more were effective. At the 95% confidence interval, the reduction in carrot eaten when fresh prills were used, ranged from 10% to 36%.

Note that no evidence was found for a carry-over effect from the age of prill experienced by a rabbit on the previous occasion of testing.

Thus, it appears that the fresh prills did have an effect on the preference of the rabbits, although there was no evidence that prills weathered for two weeks or more were effective.

Conclusions & Recommendations

There is strong evidence to suggest that garlic is effective, when presented as fresh prills, at deterring the majority of rabbits from eating carrot when carrot free from garlic odour is also available. However, there is no evidence that this response will continue once the prills have been weathered during the autumn and winter, for two or more weeks.

Based on the consistent and outstanding results with fresh prills, it is recommended that a similar experimental trial is conducted, but at a higher percent garlic dose per prill, which may counter the apparent deterioration by weathering, and thus extend the longevity of this response. Specifically, the percentage of garlic juice concentrate in the prills could be increased to 11% or 22%. Increasing the prill density from 12 Kg ha$^{-1}$ to 20 Kg ha$^{-1}$ or higher (maximum density of 150 Kg ha$^{-1}$) may not achieve the increased longevity if the prills are equally exposed to the weather?

Example 2

Use of Garlic Juice Concentrate (NEMguard®) Against PCN (Potato Cyst Nematode-*Globodera Pallida*)

NEMguard® is a garlic juice concentrate which acts as a powerful nematicide.

A sequence of developmental work with NEMguard® formulations has identified clear evidence of nematicidal effects against both free living and cyst nematodes.

The liquid formulation of NEMguard® in particular lends itself to delivery through trickle feed irrigation and preliminary work conducted on potato crops produced very encouraging results, with a 14% increase in gross yield attributed to two applications of NEMguard®. This non-public trial was in a field with a significant Potato Cyst Nematode (PCN) population.

In-vitro work has enabled the inventors to further develop the field protocol. The protocol on product use rate is presented below.

1.0 Strength of Use of Solutions

It has been shown that solutions of the garlic juice concentrate (NEMguard®) as dilute as 0.05% v/v produce almost total kill within 24 hrs. With 0.1% v/v solution strengths total kill can be achieved in 4 hrs. With 0.25% v/v solution strength, total kill can be achieved in 1 hr. Use of the concentrate should therefore be planned to operate within these three dilutions as a balance between efficacy and cost.

Option 1 (Timed)

If it is assumed that the concentrate is added to a 1000 liter volume at the end of an irrigation sequence, then the following ratios of volume addition are needed.

@ 0.05% v/v in 1000 liters=0.5 liter NEMguard®
@ 0.1% v/v in 1000 liters=1.0 liter NEMguard®
@ 0.25% v/v in 1000 liters=2.5 liter NEMguard®

Ideally the percolation time for the last 1000 liters should be managed to maximise persistence in the soil volume expected to contain migrating PCN. Clearly addition at the end of the sequence reduces elution of the product away from the primary target. It is assumed that soil at or close to field capacity, will show reduced drainage, thereby enabling the delivery dose to be maintained for as long as possible.

It is preferable to mix the NEMguard® with the last 1000 liters of water prior to pumping out. If this is not possible, then the NEMguard® should be added to the pipe work over a period of several minutes to increase the chances of adequate mixing.

Option 2 (General)

If we assume that the garlic juice concentrate (NEMguard®) is to be added over the entire irrigation delivery event ~9000 liters over 1-2 hrs, the following volume additions need to be considered:—

@ 0.05% v/v in 9000 L=4.5 liters
@ 0.1% v/v in 9000 L=9.0 liters
@ 0.25% v/v in 9000 L=22.5 liters Consideration of the two delivery approaches, timed and general identifies single event use rate volumes of between 2.5 l and 22.5 l as likely to give evidence of efficacy.

In view of the rapidity with which NEMguard® kills nematodes the overall approach should be maximisation of peak dose, whilst minimising water volume on the grounds of economics.

The permutations increase considerably if the total rate/ha is increased thereby making more product available.

2.0 In Conclusion

The $LD_{50}$ of NEMguard® for free living nematodes has been independently determined at ~0.025% v/v. This clearly gives considerable scope for product delivery strengths substantially above this value whilst still being economic relative to other nematicides.

The rapidity with which NEMguard® kills favours "bursts" of relatively high solution strength that could be managed to persist by being added at the back end of an irrigation event.

This approach also allows several repeat applications at for example weekly intervals for six weeks.

The alternative is to apply the product as a single high dose through an entire irrigation event.

If management and infrastructure of the system allow, multi burst approach should be considered.

3.0 Schematic Protocol

Assume 9000 l delivered in 1-2 hrs. 1000 liters take 6.6 minutes to pump (1 hr rate)

1 Pump 7000-8000 liters of normal water in to crop.
2 Add 2.5-5 L NEMguard® to last 1000 liters, this is ~53 mins (6.6 mins left)
3 Pump out
4 If addition of NEMguard® tales 2 mins, then last pulse is diluted in ~660 liters which should be adequate to distribute the product.
5 Repeat weekly for either 3-6 weeks depending on solution strength used and total rate/Ha selected.

Example 3

Effectiveness of the Garlic Concentrate and Granules Impregnated with the Concentrate Against Nematodes 3.0 Summary A programme of non-public field trials in potato and root vegetable crops has identified commercially significant levels of damage reduction where the proposed formulations formulations (NEMguard®) have been applied to control nematodes.

The main body of evidence is derived from the use of granular products applied at drilling, when compared to the efficacy of products such as Temik. A limited number of trials have been carried out by independent organisations approved by the Pesticide Safety Directive, or similar organisations accredited in their own country (South Korea). Conclusions in these reports support the claim that NEMguard® has nematacidal properties.

The most advanced formulation, in granular "NEMguard" form, appear well suited as an alternative to Temik and Vydate in root vegetables.

There is a high degree of consistency within the in-vitro and field experimentation.

3.1 Preliminaries

In the time that the inventors have been examining garlic products for use in crop protection, the potential for a formulation as a nematicide has become increasingly clear. A combination of in-vitro primary screening and replicated non-public field trials in potato, parsnip, carrot and melon crops in Europe and Korea has provided evidence that nematodes can be killed by the chemicals in the garlic products (NEMguard®). Plants in the field appear to respond to sub-surface applications of the granules and liquids with significant increases in vigour and gross yield, which appear to relate to nematicidal effects.

In the case of root vegetables such as carrot there is clear independent evidence that quality issues such as root forking and stunting caused by free-living nematodes can be significantly reduced from a single application of NEMguard® granules applied at drilling.

Controlled experiments in vitro and controlled bioassays in vivo with *Longidorus elongatus* and *Globodera rhostochiensis* also provide evidence that NEMguard® is a powerful nematicide with efficacy comparable to that seen with Temik.

The European review of pesticide active ingredient is expected to lead to the removal of approximately 66% of the presently approved active substances by around 2007. Nematicide products such as Aldicarb are already under intense scrutiny. Derogation has been granted for its use in approved crops up until 2007.

There is therefore a huge opportunity for environmentally benign products that have nematicidal/nematistatic activity to replace those highly toxic products such as aldicarb, vydate and methyl bromide 3.2 Introduction to the Program The preliminary bio-assay work with garlic against nematodes was carried out in 1998. This work involved dissolving prototype ECOguard granules formulated with garlic juice concentrate in water and then introducing specimens of various plant parasitic nematode species into the supernatant. Without exception all species were killed at solution strengths of 2.5% w/v granule to water in 2 hrs.

In the case of *Globodera pallida* (PCN) and *Longidorus elongatus* (root fanging), mortality reached these levels in four hours with solution strengths of 1.25% w/v. In the case of *Longidorus* spp. significant mortality occurred at 24 hrs with solution strength's of 0.25% w/v.

Since these primary screening experiments, the inventors have maintained a research and development programme on nematology, through a combination of non-public field trials and further in-vitro research.

The data from both in-vitro and field scale usage of the formulations has clearly identified nematicidal properties at use rates that are economic. This is particularly the case where granules have been applied to crops of root vegetables such as carrots and parsnips to protect them from free-living and cyst nematode damage.

3.3 Results

TABLE 3.3.1

Effects in vitro, percentage mortality (SCRI 1998). First experiments with garlic juice concentrate (NEMguard ®)

| Nem species | Rate of product | | | |
| --- | --- | --- | --- | --- |
| | 2 hrs Contact | 4 hrs Contact | 6 hrs Contact | 24 hrs Contact |
| *Paratrichodorus* | | | | |
| 2.5% | 100 | 100 | 100 | 100 |
| 1.25% | 0 | 100 | 100 | 100 |
| 0.25% | 0 | 0 | 4 | 14 |
| Control prill | 0 | 0 | 0 | 0 |
| *Golbodera* | | | | |
| 2.5% | 100 | 100 | 100 | 100 |
| 1.25 | 98 | 100 | 100 | 100 |
| 0.25% | 7 | 13 | 18 | 72 |
| Control prill | 0 | 0 | 0 | 0 |
| *Longidorus* | | | | |
| 2.5 | 100 | 100 | 100 | 100 |
| 1.25 | 77 | 100 | 100 | 100 |
| 0.25 | 3 | 4 | 34 | 58 |
| Control prill | 0 | 0 | 0 | 0 |

The data above clearly shows that there is a toxic material to nematodes in the "NEMguard ®" formulation.

Figure 2:
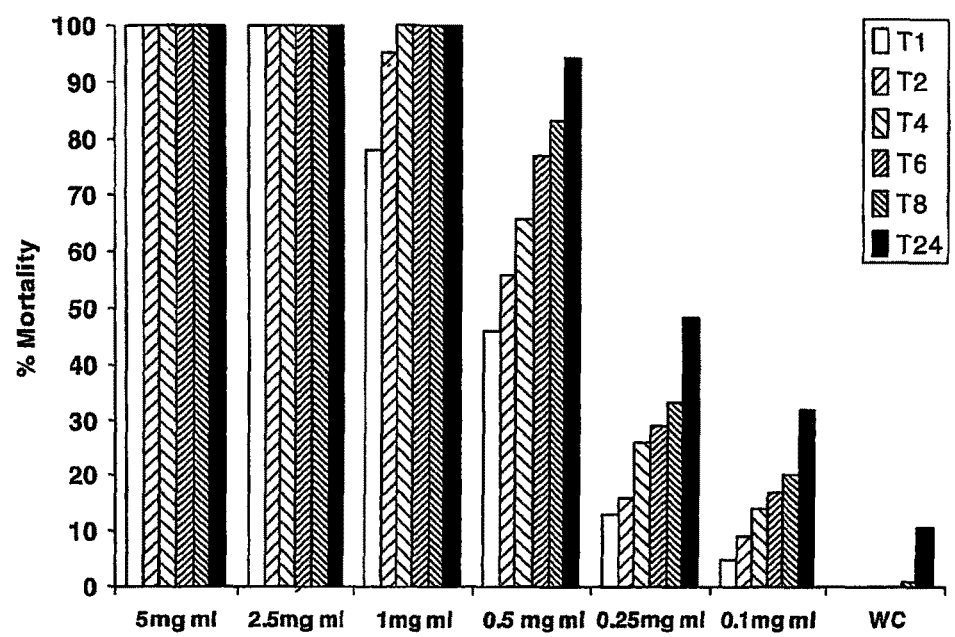
FIG. 2 is a graphical representation of the results of in-vitro bioassay of the garlic juice concentrate against *Longidorus elongatus*.

This result was confirmed, when garlic juice concentrate was used in an in-vitro bioassay comparing rate of kill against solution strength. FIG. 2 is a graphical representation showing the; in-vitro bioassay of the garlic juice concentrate against *Longidorus elongatus*. Mortality is grouped according to contact time (1-24 hrs) at the various dilutions.

The data indicates that the $LD_{50}$ at 24 hrs is ~0.025%.

3.4 Impact of the Granules on Free-Living Nematodes

The non-public field trials in potato crops provided evidence of an impact on PCN as rate of application increased. When NEMguard® was applied to crops of root vegetables, the impact of the product can be assessed through differences in the amount and type of root malformations attributed to nematode feeding.

The UK root vegetable industry relies very heavily on Temik as a means of reducing root damage and promoting yield in crops of carrot and parsnip. In 2003, the inventors initiated a program of non-public field trials to evaluate the potential for NEMguard® to replace Temik in these vegetable crops.

When root vegetable crops are established, Temik is co-applied with the seed into the same furrow and offers protection to the emerging radicle. Nematodes attack the delicate new root tip, which leads to root forking and stunting, with a consequential loss of quality and yield. The impact of free-living nematodes can be such that entire crops become uneconomic to harvest.

3.4.1 Parsnip Crop-at Hainford (Norwich)

In non-public trials at Hainford (Norwich), the inventors laid out an 8 replicate, 6 treatment randomised block, with Temik included at a rate that reflected commercial best practice. NEMguard® was included at four rates: 5, 10, 15 and 20 kg/ha and all these were referenced against an untreated control. All applications were made through a commercial seed drill with standard granular applicator. The site had been tested for nematode populations and was considered to be at risk of damage, with Temik applications justified.

The crop was assessed at an intermediate stage in maturity and the proportion of forked and fanged roots determined.

Figure 3:
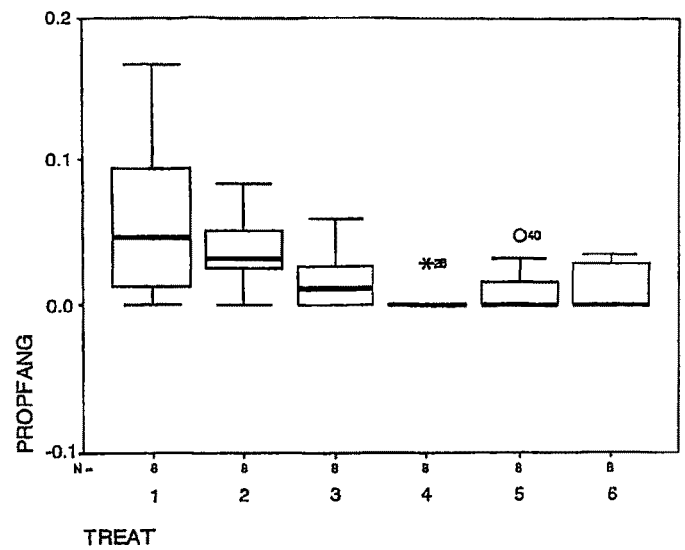
FIG. 3 is a graphical presentation of the proportion of root fanging in a parsnip crop with various treatments.

A significant difference in root fanging occurred within the treatments, this is illustrated in FIG. 3, which shows root forking in parsnip crop at Hainford (Norwich).

The boxes (FIG. 3) represent the inter-quartile ranges, which contains 50% of values. The whiskers are lines that extend from the box to the highest and lowest values across the replicates, excluding outliers. A line across the box indicates the median. Treatments are significantly different.

Treatment
1=Control
2=Temik (aldicarb)
3=NEMguard® 5 kg/ha
4=NEMguard® 10 kg/ha
5=NEMguard® 15 kg/ha
6=NEMguard® 20 kg/ha The control (treatment 1) had significantly more forked and fanged roots than all the NEMguard® treatments (3-6), 5-20 kg/ha respectively. The NEMguard® treatments at 10-20 kg/ha were significantly better than Temik. At this trial site there was also evidence of increased plant stand with increasing NEMguard® applications (FIG. 4)

Figure 4:
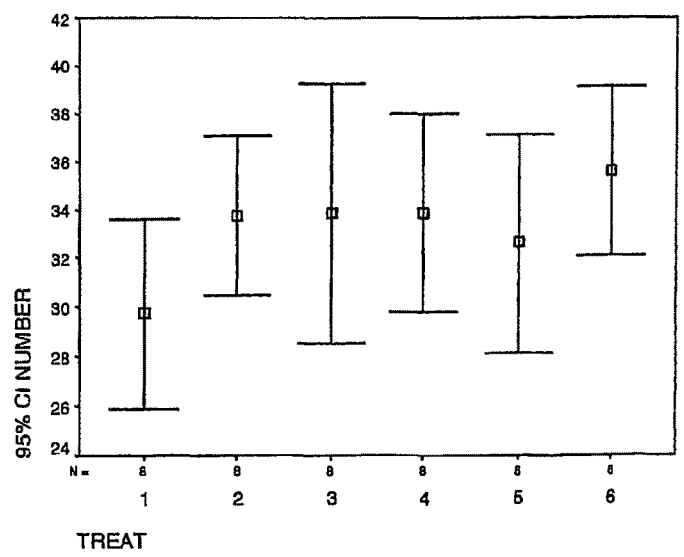
FIG. 4 is a graphical presentation of plant stand with increasing applications of garlic concentrate.

FIG. 4—Plant stand in relation to treatment.

The bars represent the range of values from individual replicates. The Temik and all NEMguard® applications appear to increase plant stand over the control. The 20 kg/ha rate of NEMguard® almost separates from the control.

Taken together, the data on root forking and plant stand numbers are good evidence that NEMguard® was as effective as Temik in defending the crop from plant loss and root damage.

3.5.1 Carrot Trial Posketts Farm, Yorkshire

A complimentary trial to that on the parsnips was run on carrots. This non-public trial compared the effect of 20 kg/ha rates of NEMguard® against Temik applied at a rate reflecting commercial best practice. All treatments were referenced against an untreated control. The site was selected on the basis of nematode numbers determined from soil sampling.

The trial was laid out in three replicates with all treatments applied through a conventional tractor mounted drill.

Table 3.5.1 Impact of NEMguard® on Root Forking and Stunting. Summary of Trial Results at Posketts Farm, Yorkshire 4 Replicate, randomised block
1 Control
2 Temik
3 Standard ECOguard® 20 kg/ha Percent of Fanged and Stunted Roots in Each Replicate.

|  | Control | Temik | EG (standard) |
|---|---|---|---|
| Block 1 | 3.2 | 3.0 | 4.8 |
| Block 2 | 11.1 | 4.4 | 2.8 |
| Block 3 | 16.8 | 7.7 | 7.8 |
| Block 4 | 8.6 | 9.0 | 4.5 |
| Mean/rep | 9.92 | 6.02 | 4.97 |

Total Number of Roots Sampled/Treatment

| 441 | 505 | 421 |
|---|---|---|

A statistical analysis of the data did not reveal significant differences between treatments. The data does have some clear trends, with the control having ~50% more fanged and stunted carrots than the other treatments. The large number of roots examined/treatment adds further confidence to the robustness of the effects.

Figure 5:
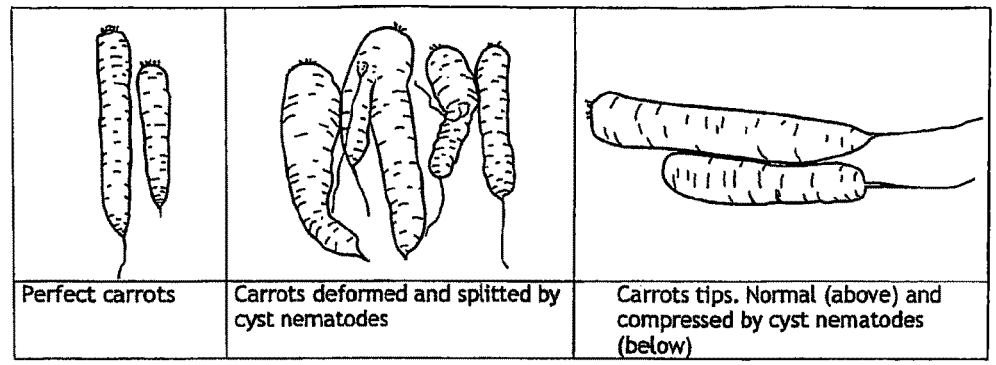
FIG. 5 shows the types of deformation caused by cyst nematodes i.e. small carrots with compressed tips, split and deformed carrots.

Drawings illustrating the symptoms seen across one of the blocks are given in FIG. 5.

The trial provided good evidence that NEMguard® formulations significantly reduced root forking and stunting to at least the extent noted with Temik in the same trial.

3.5.2 Further Trial Results Relating to Prevention of Root Fanging in Carrots Caused by Nematodes.

In response to pressure to find alternatives to Temik, a group of non-public trials was run to compare and contrast the efficacies of Temik, Vydate, Nemathorin and Nemguard. The trials on carrots were spread over three sites in Norfolk, Yorkshire and Nottinghamshire and included NEMguard® at 20 kg/ha applied at drilling. A summary table of the percentage of root forking at each site is given below in table 3.5.1

All sites had been specially selected on the basis of populations of free-living nematodes in soil samples.

TABLE 3.5.2

Relative differences in percentage of root forking in 3 carrot crops.

| Product | Rate/ha | Trial 1, Notts | Trial 2, Norfolk | Trial 3, Yorks | Means across all trials |
|---|---|---|---|---|---|
| Untreated |  | 14.3 | 17.2 | 14.1 | 15.2 |
| Temik | 8.45 | 6.3 | 6.0* | 13.7 | 8.6 |
| Vydate | 13.75 | 9.3 | 10.4 | 11.0 | 10.2 |
| Vydate | 20.0 | 9.2 | 8.4 | 15.2 | 10.9 |
| Vydate | 25.0 | 7.5 | 6.6* | 14.9 | 9.6 |
| Vydate | 55.0 | 9.0 | 9.4 | 9.1 | 9.2 |
| Nemathorin | 17.8 | 14.3 | 8.7 | 10.6 | 12.2 |
| NEMguard ® | 20.0 | 11.2 | 4.7* | 12.8 | 9.6 |

*Significantly better then control

Significant treatment effects occurred at the Norfolk site, where NEMguard® was the most effective treatment, reducing root forking by 73%. In contrast, Temik reduced root forking by 65%. Collectively across all the three trial sites, NEMguard®, Temik and Vydate (at all rates) exerted very similar levels of control.

3.5.3 Trials with NEMguard® Against Carrot Cyst Nematode

The inventors conducted a group of non-public pot experiments with carrots planted in field soil with a history of producing crops affected by yield and quality loss attributed to the activities of carrot cyst nematodes *Heterodera carotae*.

When these experiments were assessed, there was evidence of a treatment and dose affect on symptoms caused by carrot cyst nemtodes. NEMguard® applications at a rate equivalent to 30 kg/ha appeared superior to any other treatment.

A non-public field scale study was initiated following the pot experiment, where four rates of NEMguard®, 10, 20, 30 and 40 kg/ha were compared to an untreated control. This trial was assessed independently and produced a clear treatment and dose effect of economic importance. All NEMguard® applications increased saleable yield in the trial. The greatest gain occurred with NEMguard® applied at 20 kg/ha, which increased total yield by 12.6 tons/ha.

The effects of NEMguard® in the field trial are shown in table below. The number of saleable roots also increased with 10-30 kg/ha ECOguard®.

With the following assumptions use of ECOguard® in carrots offers substantial economic gain:

The average harvest in the autumn is 100 tons/ha.
The average sale price pr kg is 0.78 Dkr.
Approximately 1,000,000 carrots pr hectare with an optimal weight of 100-gram pr carrot.

TABLE A

The economic benefit of using ECOguard ® in Lammefjorden carrots.

| Treatment | Saleable carrots (tons/ha) | Extra yield (tons/ha) | Total weight (tons/ha) | Extra yield (tons/ha) | Total extra yield (tons/ha) |
|---|---|---|---|---|---|
| 0 kg | 69.4 | — | 75.0 | | |
| 10 kg | 73.4 | 4.0 | 76.6 | 1.6 | 5.6 |
| 20 kg | 76.2 | 6.8 | 87.6 | 12.6 | 19.4 |
| 30 kg | 78.5 | 9.1 | 86.3 | 11.3 | 20.4 |
| 40 kg | 73.1 | 3.7 | 79.8 | 4.8 | 8.5 |

The data in table A, above, clearly identifies a dose response, with optimal effects seen at 20 kg/ha of NEMguard ®.

Example 3A

Non-Public Trial with Carrot Cyst Nematode

Purpose:
The purpose of the trial was to observe a possible dose-response on the attack of the carrot cyst nematodes, in order to determine the optimal dose to be used in a field trial.
Crop:
Carrots $F_1$ CR 501. Coated with Thiram.
Trial Start:
15 Jan. 2004
Trial Assessment:
7 Apr. 2004 & 11 May 2004.
Plots:
10 rows of pots per treatment. No replications.
Plants:
10 seeds per pot
Treatments:
Untreated
10 kg/ha=14 granules/pot=50 mg/pot
20 kg/ha=28 granules/pot=100 mg/pot
40 kg/ha=56 granules/pot=200 mg/pot
80 kg/ha=112 granules/pot=400 mg/pot
Seeds and granules were covered with approx. 0.5-1 cm soil in the pots.
Results:
At the first assessment in the beginning of April there was a big difference in the appearance of the roots between the different treatments. The untreated carrots had less white roots than the carrots treated with 10-80 kg/ha. There was no visible difference on doses. The carrots were very small and it was decided to wait another month before the final assessment.

It was not possible to make a statistical analysis in this screening trial because there were only 10 pots per treatment. The results can therefore only show a tendency of what can be expected in the field.

TABLE 1

The results divided among treatments.

| | Treatments (kg/ha) | | | | |
|---|---|---|---|---|---|
| | 0 | 10 | 20 | 40 | 80 |
| Average Number of cyst | 14.4 | 12.7 | 9.1 | 6.6 | 8.3 |
| Average length of the longest leaf | 11.28 | 11.00 | 12.67 | 12.78 | 11.83 |
| Average Vigour score | 2.33 | 2.11 | 2.89 | 3.33 | 3.11 |

Vigour Score:
1: Poor
2:
3:
4: The best plants
Number of Cyst:
The number of cysts was roughly counted per carrot. An average of the number of cysts for all the plants per pot was estimated.

The number of cysts seemed to decrease with increased doses of garlic concentrate. The length of the longest leaf and the vigour of the plants tended to increase with increasing the dose. The dose of 80 kg/ha may be phytotoxic because the length of the leaves and the vigour score decreased compared to the previous doses but at the same time it seemed the number of cysts increased.

TABLE 2

The average number of cyst and the length of the longest root divided among categories.

| | Category of vigour | | | |
|---|---|---|---|---|
| | 1 | 2 | 3 | 4 |
| Average number of cyst | 16.00 | 10.7 | 8.8 | 9.1 |
| Average length of the longest leaf | 10.8 | 11.2 | 11.8 | 13.08 |

It can be seen from table 2, that the number of cysts decreased markedly from the poorest category 1 to the best category 4. The average length of the longest leaf increased though the categories.

The figures in table 2 confirmed the visible difference observed between the plants.

TABLE 3

Percent of pots in each category of vigour (9 pots pr treatments)

| | Treatments (kg/ha) | | | | |
|---|---|---|---|---|---|
| | 0 | 10 | 20 | 40 | 80 |
| Category 1 | 22% | 11.1% | 11% | 0% | 11% |
| Category 2 | 30.3% | 66% | 11% | 22% | 11% |
| Category 3 | 31.3% | 22% | 55.5% | 22% | 33.3% |
| Category 4 | 11% | 0% | 22% | 55.5% | 44.4% |

It can be seen from table 3, that the majority of good vital plants moved from category 2 to category 4 with the increased dose from 10 to 40 kg/ha. With 10 kg/ha there were no plants in category 4. With 40 kg/ha there were no plants in category 1 but more than half the plants were in category 4. Thus, there was a tendency for more vigorous plants with increasing dose of ECOguard. It can be seen that 80 kg/ha wasn't as good as 40 kg/ha.

Conclusion:

A dose-response was observed.

The number for carrot cyst nematodes decreased with the application of 10-40 kg/ha.

The vigour and the length of the longest leaf increased with the application of 10-40 kg/ha.

The highest number of pots in high categories for vigour (3-4) was found with the application of 20-40 kg/ha.

The optimal dose for carrot cyst nematodes is probably 20-40 kg/ha.

Example 3B

Further Results Showing the Efficacy of Garlic Concentrate Impregnated Granules Against Cyst Nematodes in Carrots Background:

In Lammefjorden on Sealand, carrots have been grown for many years because the soil is rich in nutrients and have an ideal structure for carrots. Unfortunately the many years on the trial site of carrot production have increased the pest pressure of cyst nematodes to such a degree that carrot production on many soils is impossible.

Purpose:

The purpose with of the trial was to investigate if the attack from cystenematodes in late carrots could be decreased/reduced.

Trial Plan:

In non-public trials, one hectare of infected nematode soil was divided into 6 rows and drilled with carrots seeds and ECOguard Granules. There were two untreated rows. 6 plots per row with carrots were dogged up and measured (approx 80-100 carrots pr plot).

| Treatments: | 0 kg/ha | 10 kg/ha | 20 kg/ha | 30 kg/ha | 40 kg/ha | 0 kg/ha |
|---|---|---|---|---|---|---|

The carrots were drilled and treated on the Dec. 5, 2004. The trial was assessed on the Sep. 25, 2004.

A band of one meter with four rows was dogged up, sorted, counted and weighed. A growth difference could be seen between untreated and 20-30 kg ECOguard/ha.

Results:

TABLE 2

The number of good and bad carrots.

| Number | No. of good carrots | % Increase in good carrots | No. of bad carrots | Total no. of carrots |
|---|---|---|---|---|
| 0 kg | 48.67 | | 37.83 | 86.50 |
| 10 kg | 59.33 | +15.7 | 38.33 | 97.67 |
| 20 kg | 48.17 | −1.0 | 27.00 | 75.17 |
| 30 kg | 58.00 | +19.2 | 26.00 | 84.00 |
| 40 kg | 51.17 | +5.1 | 34.33 | 85.50 |

The number of good carrots increased with an application of 10 to 30 kg/ha ECOguard. The treatment with 20 kg/ha had approximately the same number of carrots in the rows as the untreated carrots. There is no explanation for the diminished number of carrots.

10 and 30 kg/ha ECOguard gave 16-20% more saleable carrots. The number of bad carrots decreased. The total number of carrots increased on average by 11 carrots per one-meter row.

There is a tendency that the carrots respond with phytotox to the application of 40 kg/ha ECOguard. It can be seen in the table above and in the tables below that 40 kg/ha doesn't improve the quality of the carrot.

FIG. 4 shows the types of deformation caused by cyst nematodes i.e. small carrots with compressed tips, split and deformed carrots

TABLE 1

The weight of good and bad carrots.

| Treatment | Weight of good carrots (g) | Weight of bad carrots (g) | Total weight (g) | % Weight increase |
|---|---|---|---|---|
| 0 kg | 4494.08 | 1964.17 | 6458.25 | — |
| 10 kg | 5391.00 | 1950.83 | 7341.83 | +13.7 |
| 20 kg | 4922.33 | 1545.50 | 6467.83 | +0.15 |
| 30 kg | 5583.33 | 1529.83 | 7113.17 | +10.1 |
| 40 kg | 4921.17 | 1820.17 | 6741.33 | +4.4 |

The weight of the good carrots increased from 10 to 30 kg/ha. The total weight increase was 10-13.5%. Again 20 kg/ha doesn't fit into the trend.

TABLE 2

The average number of roots per plot, average root weight, percentage increase in average root weight and percentage saleable carrots.

| Treatment | Average number of roots pr plot | Average root weight (g) | % Increase in average root weight | % Saleable carrots |
|---|---|---|---|---|
| 0 kg | 86 | 75.0 | | 69.4 |
| 10 kg | 94 | 76.6 | +2.1 | 73.4 |
| 20 kg | 76 | 87.6 | +16.7 | 76.2 |
| 30 kg | 84 | 86.3 | +15.0 | 78.5 |
| 40 kg | 89 | 79.8 | +6.5 | 73.1 |

It can be seen that the average number of roots pr plot was highest for 10 kg/ha. The lowest number of carrots was with 20 kg/ha. Perhaps the drill didn't drill the seeds properly. There was no significant difference between 0, 10, 20, 30 & 40 kg/ha.

The average root weight increased with 10-30 kg/ha. The increase was between 15-17% root weight.

The number of saleable roots increased with 10-30 kg/ha ECOguard.

TABLE 3

The economic benefit of using ECOguard in Lammefjorden carrots.

| Treatment | Saleable carrots (tons/ha) | Extra yield (tons/ha) | Total weight (tons/ha) | Extra yield (tons/ha) | Total extra yield (tons/ha) | Gross margin Dkr/ha |
|---|---|---|---|---|---|---|
| 0 kg | 69.4 | — | 75.0 | | | |
| 10 kg | 73.4 | 4.0 | 76.6 | 1.6 | 5.6 | 4,370.00 |
| 20 kg | 76.2 | 6.8 | 87.6 | 12.6 | 19.4 | 15,130.00 |

TABLE 3-continued

The economic benefit of using ECOguard in Lammefjorden carrots.

| Treatment | Saleable carrots (tons/ha) | Extra yield (tons/ha) | Total weight (tons/ha) | Extra yield (tons/ha) | Total extra yield (tons/ha) | Gross margin Dkr/ha |
|---|---|---|---|---|---|---|
| 30 kg | 78.5 | 9.1 | 86.3 | 11.3 | 20.4 | 15,910.00 |
| 40 kg | 73.1 | 3.7 | 79.8 | 4.8 | 8.5 | 6,630.00 |

The average harvest in the autumn is 100 tons/ha.
The average sale price pr kg is 0.78 Dkr.
Approximately 1,000,000 carrots pr hectare with an optimal weight of 100-gram pr carrot.

Conclusion:

There was a clear tendency for reduction of cyst nematode attack in carrots.

The number of saleable carrots increased with 17% with 30 kg ECOguard/ha and the average root weight increased from 75 gram to 86 gram. An optimal carrot weights 100 gram.

The carrots were only treated once at drilling—the optimal doses are 2-3 treatments during the growing season with either granule or liquid form garlic concentrate. For example granules at drilling and liquid during the growing season.

Example 4

7.3 ECOguard as a Nematicide 7.3.1 Carrot Trial

Figure 6:
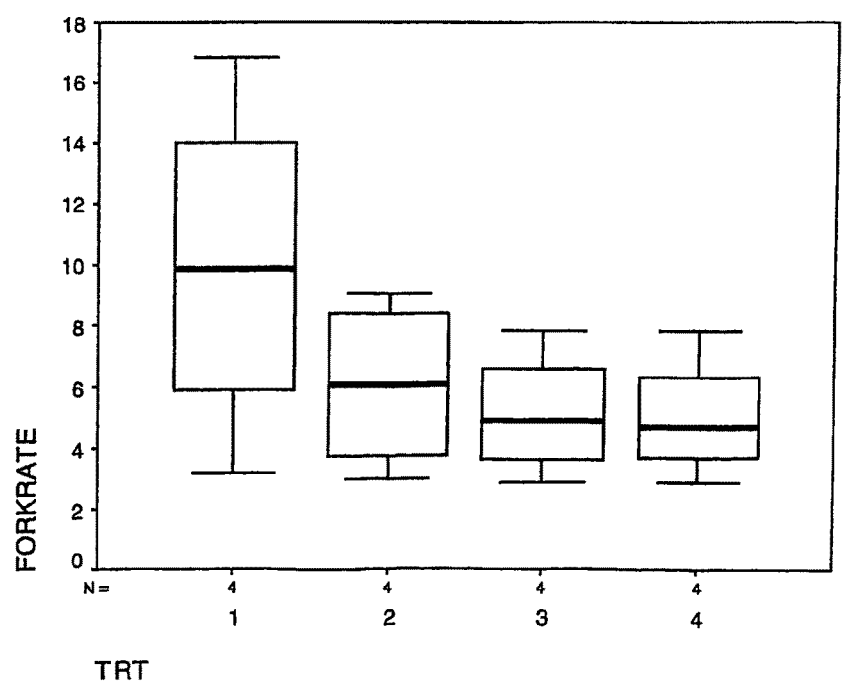
FIG. 6 shows the effect of treatments on the rate of carrot forking.

Data from the non-public carrot trial at Posketts (see example 3) has been analysed and shows a clear trend towards reduction in root forking where NEMguard granules had been applied at time of drilling. The magnitudes of effects are illustrated graphically in FIG. 6, where the treatment against the rate of forking is shown.

Treatment 1 is the control, treatment 2 is Temik and treatments 3&4 are 20 kg/Ha application of NEMguard granules. The 2 NEMguard applications are almost statistically separate from the control and very similar to the pattern of data seen at Hainford with respect to parsnips (see example 3). At the very least, NEMguard and Temik appear to produce similar levels of effect within the two crops.

7.3.2 PCN at Needham Field, Yaxley

Following a report on apparent gross yield increase where NEMguard granules and CL AIL 0021 liquid (garlic concentrate) were used in combination, the field was re-sampled in order to determine the residual PCN egg/gram at the end of the crop production cycle. These results have been compared to the initial egg/gram data and are presented below in table 7.3.2.

TABLE 7.3.2

PCN numbers at Needham Field, Yaxley

| Sector/treatments | Initial egg/gram | Final eggs/gram | Fp/Ip ratio |
|---|---|---|---|
| 1 granules + liquid | (15) | 0 | 0 |
| 2 granules only 30 kg | 16 | 5 | 0.3 |
| 3 granules only 30 kg | 18 | 1 | 0.05 |
| 4 granules + liquid | 35 | 46 | 1.31 |

The data in table 7.3.2 above does suggest a high degree of inhibition of PCN reproduction.

The most important data observed is in sector 4 where there was a commercially very significant population of PCN found at the start of cropping. The re-sample data also confirms the presence of a high PCN population in this sector, but the rate of increase in the population due to the potato crop appears to have been minimal and is essentially the same as that found at the start. This is a very significant result as use of nematicides in potato crops is primarily to inhibit PCN reproduction and ideally keep the population of egg/gram as close to that at the commencement of the crop.

An Fp/Ip ratio of 1.31 would normally be acceptable to the Pesticides Safety Directorate (PSD) as proof of nematicidal effects.

7.3.3 Root Knot Nematode Control in Sun Melons (Korea)

In non-public trials, the efficacy of NEMguard (granules impregnated with the garlic concentrate) and CL AIL 0021 liquid (the garlic concentrate) as nematicide to root knot nematodes has been evaluated.

The resulting report states that significant differences with treatments vs. the control were found, with all ECOguard formulations being statistically equivalent to Carbofuran.

In conclusion, the report states "Compared to Carbofuran Eco-guard GR and SR showed 83.5-94.9% control efficacy 30 days after treatment and 87.9-97.1% control efficacy (after 60 days) without phytotoxicity. Therefore the products can be used as a nematicide to root-knot nematode *Meloidogyne* spp., on orient-melon"

A re-evaluation of the data suggests that due to irregular distribution of initial nematode numbers in the treatment replicates at the start, the degree of efficacy compared to carbofuran may be less than that quoted above, but nonetheless is substantial, with the 1.25% solution strength having 77% of the efficacy of Carbofuran.

Even allowing for a degree of caution in interpreting the results, the Korean data is good evidence of CL AIL 0021 formulations acting as a nematicide to a genus of widespread distribution and major economic importance.

Example 4A

Efficacy of NEMguard® Against Soil Living Nematodes in a Field Used for the Growing of Strawberries In non-public field trials, the following results demonstrate the efficacy of the garlic concentrate in controlling nematodes in a field infested with a number of different species of nematodes, said field being used for growing strawberries. If such infestations are not controlled it can result in such crops of strawberries having to be abandoned.

In Norway, the needle nematode *Longidorus elongatus* is a serious root parasite of strawberry, with a damaging threshold of 3-5-ind./250 g soil. Good fields have been abandoned due to *L. elongatus*, and in severe cases 2 crop years have been lost.

Effects of NEMguard® treatments on the growth parameters in $1^{st}$ year strawberry (cv. Polka) were studied in a field infested with *Longidorzis elongatus, Pratylenchus crenatus, Tylenchorhynchus dubius* and *Paratrichodorus pachydermus* at Marnardal, southern Norway 2005. Significant difference (S) to strawberry control noted at $P \leq 0.05$, and a tendency (t) was registered in the range $0.10 \geq P > 0.05$; Non-significant difference (NS) noted for $P > 0.10$; 2-sample test.

| TREATMENT | GROWTH RATING | NUMBER OF LEAVES | NUMBER OF RUNNERS | NUMBER OF CROWNS |
|---|---|---|---|---|
| NEMguard ® 8 g/m2 | S | S | t | NS |
| NEMguard ® 16 g/m2 | S | NS | NS | NS |
| NEMguard ® 32 g/m2 | S | S | NS | NS |

NEMguard ® is a reference to granules impregnated with the garlic juice concentrate.

Example 5

An Overview of the Efficacy Data from Field Trials with ECOguard Granules Used to Control Cabbage Root Fly Damage in Norway 1.0 Preliminaries An extensive program of non-public field trials, which included five crops of swede were carried out. The field trials design was based around multiple applications of either ECOguard® liquid (garlic juice concentrate) or granules (wood flour granules impregnated with the garlic juice concentrate) and in four out of the five swede trials was referenced against Dimethoate as a standard.

Analysis of the raw data from all the swede trials conducted by the inventors revealed significant treatment differences in cabbage root fly damage in two from five trials (Romedal and Toten). At Toten, the reduction in cabbage root fly damage led to a 28% increase in saleable yield.

Overall, Dimethoate and ECOguard® appeared to reduce cabbage root fly damage by similar levels although this was only significant at Toten.

A comparison of two trials (Toten and Ga-Fa), with similar levels of cabbage root fly damage (RDI in controls 57.33 and 68.69 respectively) but widely differing patterns of rainfall during treatment applications, clearly revealed the impact of rainfall of efficacy. Episodes of heavy and persistent rain appeared to remove any efficacious effects.

2.0 Results

The overall effects are summarised in tables below.

TABLE 1

Combined root damage index (RDI) four new sites

| Treatment | Mid-Troms | Sor Ost | Ga-Fa | Toten* | Mean | % Change |
|---|---|---|---|---|---|---|
| Control | 38.29 | 24.33 | 68.69 | 54.67 | 46.49 | — |
| Dimethoate | 40.60 | 24.92 | 65.78 | 44.33 | 43.90 | −5.8 |
| ECOguard ® | 36.29 | 24.33 | 71.67 | 42.24 | 43.63 | −6.5 |

*Significant difference from control and 3 applications of ECOguard ® granules.

TABLE 2 mean saleable yields at each site, kg/sample (cat 1 + 2, Norwegian notation, 1 = undamaged, 2 = slight damage)

| Treatment | Mid-Troms | Sor Ost | Ga-Fa | Toten | Mean | % Change |
|---|---|---|---|---|---|---|
| Control | 5.29 | 19.87 | 7.78 | 11.05 | 10.99 | — |
| Dimethoate | 5.84 | 22.16 | 7.27 | 11.95 | 11.95 | +8 |
| ECOguard ® | 5.81 | 23.62 | 6.81 | 15.35 | 12.89 | +15 |

The data in table 1 and 2 above indicate a mean reduction in cabbage root fly damage associated with both Dimethoate and ECOguard®. At Toten reductions in cabbage root fly damage were significant.

ECOguard® produced the greatest gain in saleable material across the four sites, approximately doubling that seen with Dimethoate.

The corresponding data on agronomic impact of the treatments (table 2) is consistent with reduction in cabbage root fly damage increasing saleable yield. In the case of ECOguard® the mean increase in saleable yield overall was 15%, with a maximum value of 28% recorded at Toten, consistent with the corresponding significant reduction in cabbage root fly damage at this site.

A comparison of efficacy in relation to rainfall at Ga-Fa and Toten, the two trials with greatest cabbage root fly attack, shows that the loss of efficacy at Ga-Fa was almost certainly attributable to no rainfall following the first application and very heavy rainfall associated with the second and third applications.

At Ga-Fa the rainfall recorded for the 14 days covering the second and third treatment was 95.2 mm. In contrast over the same period covering the second and third treatment at Toten, the rainfall was 17.5 mm, falling mostly as light rain.

The actual rainfall records for both sites are given in table 3 below.

TABLE 3

Rainfall comparisons at Toten and Ga-Fa
Toten First treatment 30 Jun. 2004
GaFa First treatment 11 Jun. 2004
Each trial received 3 applications of ECOguard ® granules at weekly intervals

| Ga-Fa | | Rainfall | Toten | | Rainfall |
|---|---|---|---|---|---|
| 8 June | | 0.0 | 27 June | | 0.1 |
| 9 | | 3.2 | 28 | | 5.1 |
| 10 | | 1.2 | 29 | | 1.2 |
| 11 | First application | 0.0 | 30 | First application | 0.0 |
| 12 | | 0.0 | 1 July | | 1.7 |
| 13 | | 0.0 | 2 | | 19.4 |
| 14 | | 0.0 | 3 | | −0.1 |
| 15 | | 0.0 | 4 | | 0.0 |
| 16 | | 0.0 | 5 | | 8.3 |
| 17 | Second application | 0.0 | 6 | Second application | 2.0 |
| 18 | | 0.0 | 7 | | −0.1 |
| 19 | | 9.2 | 8 | | 0.0 |
| 20 | | 13.8 | 9 | | −0.1 |
| 21 | | 3.8 | 10 | | 0.1 |
| 22 | | 6.8 | 11 | | 0.1 |
| 23 | Third application | 2.4 | 12 | Third application | 0.1 |
| 24 | | 28.8 | 13 | | 1.0 |
| 25 | | 16.2 | 14 | | 0.0 |
| 26 | | 4.0 | 15 | | 0.0 |
| 27 | | 0.0 | 16 | | 0.0 |
| 28 | | 0.0 | 17 | | −0.1 |
| 29 | | 10.0 | 18 | | 15.1 |
| 30 | | 0.0 | 19 | | 0.7 |
| | | | 20 | | −0.1 |
| Total rainfall 8-30 June | | 99.4 mm | 27 June-20 July | | 55.4 mm |
| Rainfall from second application to end of period | | 95.2 mm | Rainfall from second application to end of period. | | 17.5 mm |
| Rainfall for four days preceding first application | | 4.2 mm | 6.3 mm | | |

The amount of rainfall at each site prior to the first treatment were very similar, 4.2 and 6.3 mm. However following the first application, the patterns of rainfall at each site became very different. The 10-day period following the second application is shaded for ease of comparison.

At Ga-Fa there was no rainfall for 8 consecutive days following the first application, which also covered 2 days in to the second application. Following this, there were 8 consecutive days of uninterrupted rain, with the third application being applied in the middle of this rainfall. The amount of rainfall recorded in this 8 day deluge was 85 mm.

With the first application at Ga-Fa experiencing totally dry conditions for 8 days and the second and third application then experiencing 8 and 4 days respectively of uninterrupted heavy rain, little if any effect from ECOguard® would have been expected as these represent the extremes of conditions which the inventors believe negatively impact on efficacy. The fact that each treatment experienced one or other of these extremes would completely compromise any impact on cabbage root fly. The data reflects this.

In contrast, the site at Toten experienced far more settled conditions than Ga-Fa. The first application experienced a heavy rainfall event (19.4 mm) two days after application, which probably impacted negatively on efficacy, but the second and third applications placed towards the centre of the peak of egg laying experienced 11 consecutive days of settled conditions with only very light rainfall (1 mm maximum on any single day). These conditions are considered ideal for maximising efficacy. The inventors have previously submitted data from laboratory studies that show this. The second and third applications at Toten were therefore expected to have been efficacious.

The statistical analysis of cabbage root fly damage at Toten showed that both Dimethoate and ECOguard® significantly reduced damage (P=0.004) leading to agronomically meaningful increases in saleable material from the ECOguard® treatment.

In terms of RDI, Dimethoate and ECOguard® were significantly better than control, but not significantly different to each other.

Trt 1=Control

Trt 2=Dimethoate

Trt 3=ECOguard® trt=1 subtracted from:

| Level trt | Difference of Means | SE of Difference | T-Value | Adjusted P-Value |
|---|---|---|---|---|
| 2 | −0.3100 | 0.1223 | −2.535 | 0.0302 |
| 3 | −0.3900 | 0.1223 | −3.190 | 0.0041 |

2.1 Romedal

The fifth trial site with swede was harvested earlier than the four other sites introduced in table 1 and 2.

This site experienced generally light pest pressure, but did include a group of other ECOguard® treatments applied as sprays.

The data from this trial also produced significant differences in treatments when analysed by GLIM ANOVA, with all ECOguard® treatments having lower cabbage root fly damage then the control.

This is shown below

| Kruskal-Wallis Test on C7 | | | | |
|---|---|---|---|---|
| Trt | N | Median | Ave Rank | Z |
| 1 | 75 | 0.00E+00 | 218.4 | 2.72 |
| 2 | 75 | 0.00E+00 | 175.4 | −1.13 |
| 3 | 75 | 0.00E+00 | 182.8 | −0.47 |
| 4 | 75 | 0.00E+00 | 175.4 | −1.13 |
| 5 | 75 | 0.00E+00 | 188.1 | 0.01 |
| Overall | 375 | | | |

H = 23.38
DF = 4
P = 0.000 (adjusted for ties)

All ECOguard® treatments have significantly lower (P=0.000) cabbage root fly damage than the control (trt 1). Treatment 5 is the ECOguard® granule and shows a 14% reduction in overall damage.

Presentation of the data as root damage index gives a value of 11.6 for control and 4.9 for ECOguard® granules (PSD calculation)

Although the level of attack at Romedal was low with an RDI of 11.6, a much higher level of attack occurred at Toten, with an RDI of 54.67, (higher than anything noted in controls from the UK field trials in 2004) with both of these sites showing significant reductions in cabbage root fly damage.

The one common feature at both Romedal and Toten was generally settled conditions associated with the second and third treatment applications. The rainfall data for both Toten and Romedal are presented in table 4.

TABLE 4

| Rainfall comparisons at Toten and Romedal | | | |
|---|---|---|---|
| Toten | Rainfall | Romedal | Rainfall |
| 30 June first application | 0.0 | First application | 1.7 |
| 1 July | 1.7 | | 30.2 |
| 2 | 19.4 | | 0.2 |
| 3 | −0.1 | | 0.0 |
| 4 | 0.0 | | 4.2 |
| 5 | 8.3 | | 4.5 |
| 6 | 2.0 | | 0.0 |
| 7 Second application | −0.1 | Second application | 0.0 |
| 8 | 0.0 | | 0.0 |
| 9 | −0.1 | | 0.0 |
| 10 | 0.1 | | 0.0 |
| 11 | 0.1 | | 0.2 |
| 12 | 0.1 | | 2.0 |
| 13 | 1.0 | | 0.0 |
| 14 Third application | 0.0 | Third application | 0.0 |
| 15 | 0.0 | | 0.0 |
| 16 | 0.0 | | 0.0 |
| 17 | −0.1 | | 17.9 |
| 18 | 15.1 | | 0.7 |
| 19 | 0.7 | | 0.0 |
| 20 | −0.1 | | 0.0 |
| 21 | 0.0 | Fourth application | 0.0 |
| 22 | 0.3 | | 0.7 |
| 23 | −0.3 | | 0.0 |
| 24 | 33.2 | | 3.3 |

Toten and Romedal initiated treatments on the same day in response to detection of the first cabbage root fly eggs. Treatments then followed on a weekly pattern at both sites, with Romedal having one more treatment than Toten. The first, second and third treatments at both sites were therefore synchronous and experienced very similar patterns and intensity of rainfall, which for the period associated with treatments 2 and 3 was very light at both sites.

As discussed in table 3, this contrasts with the rainfall pattern and intensity at Ga-Fa, which was very heavy and prolonged during the second and third applications.

The evidence of efficacy at Toten and Romedal appears to be very closely associated with settled conditions and episodes of light rain, with the second and third applications corresponding to a peak in egg laying.

3.0 Conclusions

Non-public field trials on swede in Norway showed ECOguard® granules produced significant reductions in cabbage root fly damage; this was irrespective of the intensity of challenge. Significant differences were seen in data sets with RDI values in the control ranging from 11.9-54.67.

The trials did not feature factorial additions of product, but it can be clearly inferred from the data on rainfall that the significant effects were largely driven by the second and third treatments being applied during the peak of pest pressure when mostly light rainfall occurred.

These conclusions are not at variance with those reached from non-public field trials in the UK if misleading trials data is restricted and collectively demonstrate a useful level of product efficacy can be obtained with well-timed applications in appropriate environmental conditions.

The maximum gain of saleable material, 28%, associated with ECOguard® granule application at Toten is considered commercially significant. In the UK such a gain would equate to ~11.2 tonnes of material, at a price of ~£200/tonne, this represents an increased return of ~£2240/ha.

The efficacy of the granules is very dependent on moisture and the time of application relative to laying of eggs by cabbage root fly.

These experiments considered the timing of application of water to granules relative to the time of placement of freshly laid eggs in the bioassay arenas.

In all two soil types were used with the following treatments replicated 10 times with 10 eggs/assay:
1. Control (water+Eggs)
2. Granules+eggs
3. Granules+eggs+water added 1 day after eggs
4. Granules+eggs+water added 30 mins after eggs
5. Granules+water+eggs added after 1 day
6. Granules+water+eggs added after 30 mins The following results were obtained:—
Percent of Hatched Eggs

TABLE 1

| Soil type | Treat. 1 | Treat. 2 | Treat. 3 | Treat. 4 | Treat. 5 | Treat. 6 |
|---|---|---|---|---|---|---|
| Natural | 95 | 81 | 80 | 12 | 59 | 4 |
| Compost | 96 | 76 | 39 | 15 | 68 | 18 |
| Mean | 95.5 | 78.5 | 59.5 | 18.5 | 63.5 | 11 |

(Treat. = Treatment)

The following results were obtained:—
Percent of Hatched Eggs

These results provide clear evidence that application of water to the granules is vital to enhance efficacy. Treatment 3, which probably most closely resembles the field situation in general, shows that where eggs and granules are present at the base of a plant, followed by a rainfall event, egg hatch is reduced by 38%. This level of efficacy can be greatly enhanced (80% reduction) if the wetting of the granules occurs soon after eggs have been placed (treatment 4). This effect is attributed to the fact that fresh cabbage root fly eggs remain permeable for a few hours after laying and the actives in ECOguard® enter the eggs more readily at this time. It is also implicit from the data above that the timing of application of ECOguard® granules in relation to pest pressure will have a major effect on efficacy (contrast treatments 5 and 6). Applications of product several days after egg laying are likely to be less efficacious that applications of product at the time of egg laying.

Example 6

Use of Garlic Concentrate in the Control of Poultry Red Mite

Figure 7:
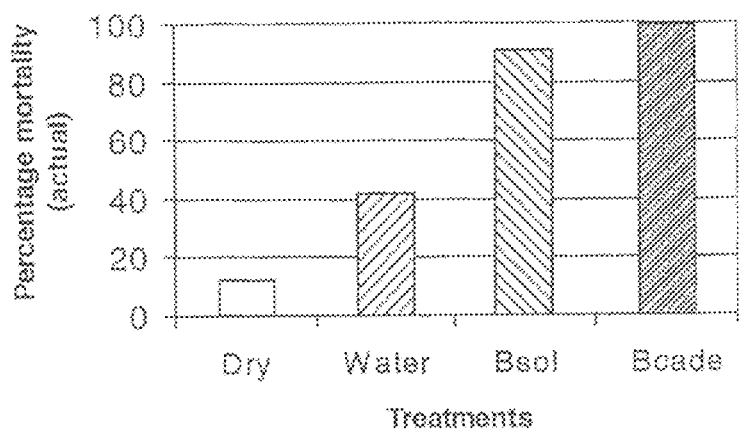
FIG. 7 shows the effect of treatments against Poultry Red Mite.

A garlic concentrate referred to as Breck-a-sol, at 3% v/v (1.5% v Garlic juice concentrate and 1.5% adjuvant oil (rape seed oil)) was applied at a rate of 189 ml/m$^2$ FIG. 7 shows results demonstrating the effectiveness of Breck-a-sol (Bsol) against Poultry Red Mite, the percent mortality of red mite is shown against controls and the use of Barricade.

Referenced against dry cell (positive control)
Water (water control)
Cypermethrin (1% v/v Barricade (Bcade) at 189 ml/m$^2$)

The results for Breck-a-Sol and Barricade were not significantly different to each other.

This pattern of data was repeated with five other experiments using mites from different sheds and different batches of garlic juice concentrate.

Also investigated were the effects of soiling (dust) on efficacy. This work showed useful product efficacy with 'moderate' levels of soiling, with efficacy of the garlic concentrate lost only at very high levels of dust soiling.

Figure 8:
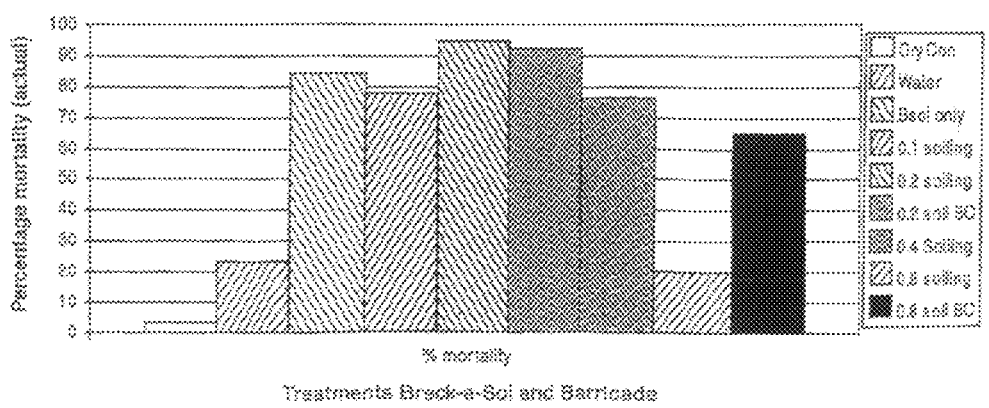
FIG. 8 shows the effect of treatment and soiling on the mortality of poultry red mite.

In FIG. 8 a series of data is presented comparing the % mortality of poultry red mite under differing levels of soiling when either Breck-a-sol or Barricade (cypermethrin) is applied as a biocide. The results from the application of Barricade are indicated on the key by BC, Dry Con=Dry control, Water=the application of water and the remaining results relate to the application of Breck-a-sol.

Soiling was applied in incremental loadings to reflect levels of soiling found on surfaces in a poultry shed.
0.1 (equivalent to ~20 g dust/m$^2$)
0.2 (equivalent to ~40 g dust/m$^2$)
0.4 (equivalent to ~80 g dust/m$^2$)
0.8 (equivalent to ~160 g dust/m$^2$)

The results show that the garlic juice concentrate (Breck-a-Sol (Bsol)) delivers a useful level of efficacy when soiling is ~80 g/m$^2$, which was not significantly different to that seen with Barricade applied to soiling at ~40 gm$^2$.

Appendix 1

HPLC Analysis

Chromatogram Data of Various Garlic Oil Samples
1. Samples:
A Garlic oil (gold standard) was analysed together with two other products—a garlic oil (industry standard) and the garlic juice concentrate.
2. Sample Preparation:
Both samples were diluted 1:10 with 100% MeCN (50 µl sample in 450 µMeCN). The garlic juice concentrate produced some white precipitate after dilution. This was removed using a 0.2 µm Target® solvent filter prior to HPLC analysis.
3. HPLC Analysis:
This was performed using an Agilent HP1100 HPLC system with diode array detection in combination with a Phenomenex C$_{18}$ (2) Luna column (250×4.6 mm, 5

μm) with a 'Securityguard' $C_{18}$ pre-column. Autosampler temperature was 4° C. and the column temperature was 37° C. and cut-off pressure was 280 Bar. Data was collected at 240 nm (with total data collected between 200-600 nm). The injection volume was found to be near optimal at 5 μl for 1:10 diluted samples. Three methods were assessed.

i. One based on a literature method (see below)—with the following modifications—Luna column and isocratic gradient of 70% MeCN (97% MeCN with 3% THF) and 30% ultra-pure water. Method time=40 min. (RBSULF1)

ii. A second method—essentially as above but using a pre-gradient step before the isocratic step. (RBSULF2)

| Time | % A (Ultra Pure Water) | % B (97% MeCN/3% THF) |
|---|---|---|
| 0 | 70 | 30 |
| 10 | 30 | 70 |
| 35 | 30 | 70 |
| 40 | 70 | 30 |
| 50 | 70 | 30 | iii. A third method (RBSULF3) based on RBSULF1 but with an extended equilibration time i.e. method time=50 min.

Method Ref:
Lawson, L. D., Wang, Z-Y. J., Hughes, B. G. (1991). Identification and HPLC quantification of the sulfides and dialk(en)yl thiosulfinates in commercial garlic products. *Planta Medica* 57: 363-370

Results: All Chromatograms at 240 nm
A. Separation
RBSULF3 Garlic Standard (5 μl 1:10)
Raw Data for Garlic Samples
Garlic Oil Gold Standard 2.5 μl injection (1:10 diluted oil)—Used as Retention Time and Peak Shape Reference Material
See FIG. 9 (Chromatogram 1)
Peak ID
(The following assignments have been made to the peaks of the chromatograms)

See FIG. 10 (Chromatogram 2-Garlic Standard)
See FIG. 11 (Chromatogram 3-Garlic Juice Concentrate)

Peak numbers are provisional, ID's based on the profile shown in the reference paper—there are several additional compounds in the standard and garlic juice concentrate that may be related compounds.

TABLE 2a

Summary Table of Product Data for a number of batches of the Garlic Concentrate
(Each Compound Expressed as μg Di-Allyl Sulfide Equivalent $g^{-1}$ Product)

| Peak No | Batch 9381 Thick Liquid | 0091 Thick Liquid | 1131 Thick Liquid | 0391 Thick Liquid | 0301 Thick Liquid |
|---|---|---|---|---|---|
| 1 | 82 | 66 | 76 | 55 | 82 |
| 2 | 131 | 136 | 153 | 104 | 93 |
| 3 | 87 | 66 | 109 | 104 | 104 |
| 4 | 579 | 579 | 546 | 409 | 442 |
| 5 | 841 | 791 | 1103 | 1026 | 1037 |
| 6 | 846 | 797 | 824 | 693 | 917 |
| 7 | T | T | 136 | 115 | 153 |
| 8 | T | T | 82 | 55 | 115 |
| 9 | 4241 | 3886 | 4181 | 4460 | 3450 |
| 10 | 360 | 448 | 415 | 289 | 464 |
| 11 | T | T | T | T | T |
| 12 | T | T | T | T | T |
| 13 | 1916 | 2233 | 1971 | 1643 | 1676 |
| 14 | 38 | 55 | 44 | 44 | 22 |
| 15 | 71 | 87 | 87 | 87 | 49 |
| 16 | 502 | 731 | 546 | 415 | 480 |
| 17 | 131 | 191 | 104 | 87 | 115 |
| 18 | 142 | 262 | 158 | 109 | 164 |
| 19 | 71 | 120 | 71 | 44 | 71 |
| Total | 10038 | 10448 | 10606 | 9739 | 9434 |
| As % of Total | | | | | |
| DAS (3) | 0.9 | 0.6 | 1.0 | 1.1 | 1.1 |
| DADS (5) | 8.4 | 7.6 | 10.4 | 10.5 | 11.0 |
| DATS (9) | 42.2 | 37.2 | 39.4 | 45.8 | 36.6 |
| 3 + 5 + 9 | 51.5 | 45.4 | 50.8 | 57.4 | 48.7 |

| | | |
|---|---|---|
| 1 = | Methyl Allyl Sulfide | $CH_3$—S—$CH_2$—CH=$CH_2$ |
| | Dimethyl Disulfide | $CH_3$—S—S—$CH_3$ |
| 2 = | Methyl Allyl Disulfide | $CH_3$—S—S—$CH_2$—CH=$CH_2$ |
| 3 = | Diallyl Sulfide | $CH_2$=CH—$CH_2$—S—$CH_2$—CH=$CH_2$ |
| 4 = | Dimethyl Trisulfide | $CH_3$—S—S—S—$CH_3$ |
| 5 = | Diallyl Disulfide | $CH_2$=CH—$CH_2$—S—S—$CH_2$—CH=$CH_2$ |
| 6 = | Methy Allyl Trisulfide | $CH_3$—S—S—S—$CH_2$—CH=$CH_2$ |
| 7 = | Dimethyl Tetrasulfide | $CH_3$—S—S—S—S—$CH_3$ |
| 8 = | Trans-1-Propenyl Disulfide | $CH_2$=CH—$CH_2$—S—S—H |
| 9 = | Diallyl Trisulfide | $CH_2$=CH—$CH_2$—S—S—S—$CH_2$—CH=$CH_2$ |
| 10 = | Methyl Allyl Tetrasulfide | $CH_3$—S—S—S—S—$CH_2$—CH=$CH_2$ |
| 11 = | Dimethyl Pentasulfide | $CH_3$—S—S—S—S—S—$CH_3$ |
| 12 = | Trans-1-Propenyl Trisulfide (Putative) | $CH_2$=CH—$CH_2$—S—S—S—H |
| 13 = | Diallyl Tetrasulfide | $CH_2$=CH—$CH_2$—S—S—S—S—$CH_2$—CH=$CH_2$ |
| 14 = | Methyl Allyl Pentasulfide | $CH_3$—S—S—S—S—S—$CH_2$—CH=$CH_2$ |
| 15 = | Dimethyl Hexasulfide | $CH_3$—S—S—S—S—S—S—$CH_3$ |
| 16 = | Diallyl Pentasulfide | $CH_2$=CH—$CH_2$—S—S—S—S—S—$CH_2$CH=$CH_2$ |
| 17 = | Methyl Allyl Hexasulfide | $CH_3$—S—S—S—S—S—S—$CH_2$—CH=$CH_2$ |
| 18 = | Dimethyl Heptasulfide | $CH_3$—S—S—S—S—S—S—S—$CH_3$ |
| 19 = | Diallyl Hexasulfide | $CH_2$=CH—$CH_2$—S—S—S—S—S—S—$CH_2$—CH=$CH_2$ |

Appendix 2

Fate and Behaviour of the Garlic Concentrate in the Environment

The formulation of the Ecoguard® granule contains 45% of garlic juice concentrate (AIL 0021) mixed with 55% of wood fibre and cellulosic binder. By far the largest component in the garlic juice concentrate (AIL 0021), the technical product, is carbohydrate. AIL 0021 is believed to comprise upto 50% carbohydrate by weight in the final product. This composition therefore produces a granule with a total composition of a 77.5% w/w mixture of biodegradable and soluble carbohydrate and cellulose.

The composition of organo-sulphur molecules in the garlic juice concentrate is predominantly molecules with di-sulpliur bridges such as diallyl-disulphide and diallyl-trisulphide believed to be in the range 3.5% w/w. These are naturally occurring compounds found in any crushed garlic.

The biological effects of the garlic juice concentrate, seen in experimentation, has not been attributed to any particular molecule or group of molecules. The biological effects noted have been attributed to the action of the product as a whole. In discussions on the general chemistry of garlic, the emphasis was on identification and quantification of some of the organo-sulphur molecules present as a means of establishing and demonstrating consistency of product during manufacturing.

The inventors believe that the residue from ECOguard® granules made from garlic juice concentrate (AIL 0021) is predominantly a mixture of biodegradable carbohydrate and cellulose derived from the woodfibre and binder carrier matrix and from pulverisation and filtration of whole fresh garlic cloves, with any organo-sulphur residue of coming from approximately 3.5% w/w of organo-sulphur compounds.

It is believed that the following arguments apply with reference to:—
Water (degradation and sedimentation/water partitioning
Soil (degradation and mobility)
Air The minor constituents of the garlic juice concentrate (AIL 0021) such as the organo-sulphur metabolites are characterised by molecules with di-sulphur bridges, which are chemically labile tending to react as electophiles, seeking out nucleophilic functional groups such as —$NH_2$; —SH; —OH; >C=O. Reaction with these functional groups breaks the di-sulphide bridge, which in the case of an aqueous reaction environment produces hydrated sulphur containing functional groups such as: —R—S—OH, where R represents one half of the di-sulphur bridge.

More specifically, HPLC analytical work on characterisation of the garlic juice concentrate (CL AIL 0021), has shown that four of the principal molecular species are: di-allyl sulphide; di-allyl disulphide; di-allyl trisulphide and di-allyl tetrasulphide. This is consistent with the breakdown of allicin to diallyl mono, di and trisulphide reported to occur at room temperature by Block 1992.

In addition, there is a high degree of similarity between the organo-sulphur chemistry of garlic and onions. Block 1992 reports, "Pioneering studies in the 1940's by Stoll and Seebeck in Basel demonstrated that the stable precursor of Cavallito's antibacterial principle of garlic (allicin) is (+)-S-2-propenyl-L-cysteine-S-Oxide (alliin). In the intact cell, alliin and related S-alk(en)yl-L-cysteine-S oxides (aroma and flavour precursors) are located in the cytoplasm and the C—S lyase enzyme allinase in the vacuole. Disruption of the cell results in release of allinase and subsequent alpha and beta-elimination of the S-oxides, ultimately affording volatile and odorous low molecular weight organo sulphur compounds such as allicin, which readily equilibrates to diallyl-disulphide and other sulphur bridged alkenes."

Four sulphoxides occur in *Allium* spp
1 S-2-propenyl-cysteine S-oxide
2 S-(E)-1-propenyl—cycteine S-oxide
3 S-methyl-cycseine S-oxide
4 S-propyl-L-cysteine S-oxide Onions contain 2, 3 and 4. Garlic contains 1, 2, and 3.

There is therefore a high degree of equivalence in the organo-sulphur chemistry between onions and garlic. In the case of onions the action of onion allinase on the precursors leads to dipropyl polysulphides as opposed to diallyl polysulphides, which dominate in garlic.

Diallyl-sulphides are considered by the inventors to be the major organo-sulphur molecules in the garlic juice concentrate (CL AIL 0021 product); this is consistent with the literature and detailed analytical results. The average concentration of diallyl-disulphide (DADS) in CL AIL 0021 calculated from 5 production batches is 12 mg/g. This therefore gives a theoretical concentration DADS in a typical Ecoguard® granules of 0.54%

The actual percentage of DADS in an Ecoguard® granule is 0.54% and for DASn 3.46%. Therefore, a 12 kg/ha application of Ecoguard® granules, applies a maximum of 65 g of diallyl-disulphide/ha and 415 g/ha DASn. It is reported by Block 1992, that garlic, onion and other members of the *Allium* spp. contain 1-5% dry weight of non-protein sulphur amino acid secondary metabolites. Given that a garlic crop may yield 20 tons/ha fresh weight and that 25% of this is dry matter, then a typical commercial crop of garlic will yield between 50-250 kg of non-protein sulphur that is to say 100-500 times more than with an application of Ecoguard® garlic granules.

On a simple gravimetric analysis a single Ecoguard® application will apply 100-500 times less organic sulphur than that which could be released into the environment from a commercial crop, if the crop was abandoned to rot down.

Given the large area of onions grown in the UK and the relative yield per hectare, Onions are a potentially much more significant source of sulphenic acids and polysulphides than garlic.

The wastage of onions at harvest is considered by the British Onion Producers Association (BOPA) to be about 12% of gross yield, which at 40 tons/ha is about 4.8 tons, this is composed of onions less than 50 mm in diameter that fall through harvesting webs. This trash will be left in the field and disked over to rot. Under these circumstances there will be a substantial release of organo-sulphur molecules into the environment. According to Block 1992 this figure could be as much as 5% of the dry matter or 60 kg/ha. In the year 2,000, around 9,000 ha of onions were grown in the UK with the total trash left in fields being estimated at 40,000 T or about 500 T of organo-sulphur compounds!

In addition BOPA estimate an additional 50,000 tonnes of onion waste per annum is generated by packers and processors, generating up to 625 T of additional organo-sulphur compounds, most of which will be disposed of to landfill, composting in waste heaps at field boundaries or by incineration again generating a similar rate of release of organo-sulphur compounds.

In each of these instances the compounds are broken down in the environment by natural processes, such as microbiological degradation, photolysis and bond cleavage by a range of electrophylic functional groups. The garlic residues in the Ecoguard® granules would be broken down by the same processes.

The inventors therefore conclude that the application of Ecoguard® granules to soil at recommended rates and by recommended methods releases significantly less organo-sulphur molecules to the soil surface than normal agricultural and food processing practices involving garlic, onion and other *allium* crops and that as there are no noticeable effects on the environment from the aforementioned standard practices then the fate in the environment issue need not be addressed in any greater detail. The same arguments also apply to the direct use of the garlic juice concentrate.

The invention claimed is:

1. A pesticide or repellent comprising a garlic juice liquid concentrate obtained from garlic juice by the removal of water from the juice by a process selected from the group consisting of:
    (i) reduced pressure distillation at a temperature below 40° C.; and
    (ii) reverse osmosis,
wherein the concentrate has a Brix value between 60 and 80; and
wherein said concentrate comprises poly-sulfides, said poly-sulfides comprising diallyl sulfide:diallyl di-sulfide:diallyl tri-sulfide:diallyl tetra-sulfide in the approximate ratios of 4%-5%:5%-8%:31%-38%:19%-22% by weight percent of the poly-sulfides present.

2. The pesticide or repellent as claimed in claim 1, wherein said concentrate comprises poly-sulfides at a concentration in the range 2 to 4% w/w.

3. The pesticide or repellent as claimed in claim 1, wherein said concentrate comprises poly-sulfides, said poly-sulfides comprising dially-sulfides of the formula RSR, $RS_2R$, $RS_3R$ and $RS_4R$ in the amount of 66%±10% by weight of the poly-sulfides present, wherein R is an allyl group.

4. The pesticide or repellent as claimed in claim 1 wherein said concentrate comprises a poly-sulfide content, and further poly-sulfides have been added to enrich the poly-sulfide content of the concentrate.

5. The pesticide or repellent as claimed in claim 4, wherein the further poly-sulfides have been added in the form of garlic oil.

6. The pesticidal composition characterised in that it comprises wood flour based granules impregnated with a pesticide or repellent according to claim 1.

* * * * *